United States Patent
Dey et al.

(10) Patent No.: US 6,463,719 B2
(45) Date of Patent: Oct. 15, 2002

(54) SUTURE WINDING MACHINE, SUTURE TRAY PACKAGE, AND METHOD OF WINDING SUTURES

(75) Inventors: Clifford Dey, Flemington; Konstantin Ivanov, Bound Brook; Martin Sobel, Flemington; Joseph Stanley Siernos, Whitehouse Station; John Rega, Milltown; David Roslon, Hillsborough, all of NJ (US); Raul Quinones, Caguas, PR (US); Alan Hughieson, Edinburgh (GB); Mehmet Reyhan, E. Windsor, NJ (US); Manfred Reiser, Hertmannsweiler (DE); Bernhard Wachter, Backnang (DE); Manfred Hild, Schorndorf (DE); Erwin Bauder, Waiblingen (DE)

(73) Assignee: Ethicon, Somerville, NJ (US)

( * ) Notice: Subject to any disclaimer, the term of this patent is extended or adjusted under 35 U.S.C. 154(b) by 111 days.

(21) Appl. No.: 09/736,007

(22) Filed: Dec. 13, 2000

(65) Prior Publication Data

US 2002/0069617 A1 Jun. 13, 2002

(51) Int. Cl.⁷ .......................... B65B 63/04; A61B 17/06
(52) U.S. Cl. .......................... 53/430; 53/116; 206/63.3
(58) Field of Search .......................... 53/430, 116, 118; 206/63.3, 339

(56) References Cited

U.S. PATENT DOCUMENTS

| | | | |
|---|---|---|---|
| 3,618,282 A | * 11/1971 | Hagel et al. | .................. 53/116 |
| 3,975,883 A | * 8/1976 | Besnyo et al. | ................. 53/116 |
| 5,271,495 A | * 12/1993 | Alpern | ....................... 206/63.3 |
| 5,438,746 A | * 8/1995 | Demarest et al. | |
| 5,469,689 A | 11/1995 | Demarest et al. | |
| 5,473,810 A | 12/1995 | Demarest et al. | |
| 5,473,854 A | 12/1995 | Demarest et al. | |
| 5,487,212 A | 1/1996 | Demarest et al. | |
| 5,487,216 A | 1/1996 | Demarest et al. | |
| 5,491,954 A | * 2/1996 | Sobel | .......................... 53/116 |
| 5,491,955 A | 2/1996 | Sobel | |
| 5,495,420 A | 2/1996 | Demarest et al. | |
| 5,500,991 A | 3/1996 | Demarest et al. | |
| 5,660,024 A | 8/1997 | Ivanov et al. | |
| 5,661,954 A | 9/1997 | Ivanov et al. | |
| 5,664,404 A | 9/1997 | Ivanov et al. | |
| 5,667,155 A | * 9/1997 | Cerwin et al. | |
| 5,695,138 A | * 12/1997 | Daniele et al. | |
| 5,788,062 A | * 8/1998 | Cerwin et al. | ............. 206/63.3 |
| 5,868,244 A | 2/1999 | Ivanov et al. | |
| 5,873,212 A | * 2/1999 | Esteves et al. | ................ 53/116 |
| 5,920,482 A | * 7/1999 | Demarest et al. | |
| 5,956,927 A | 9/1999 | Daniele et al. | |
| 5,964,075 A | 10/1999 | Daniele et al. | |
| 5,970,686 A | 10/1999 | Demarest et al. | |
| 5,983,601 A | 11/1999 | Blanch et al. | |
| 5,987,848 A | 11/1999 | Blanch et al. | |
| 6,014,851 A | 1/2000 | Daniele et al. | |
| 6,032,343 A | * 3/2000 | Blanch et al. | ................. 53/118 |
| 6,047,815 A | * 4/2000 | Cerwin et al. | ............. 206/63.3 |
| 6,076,255 A | * 6/2000 | Shikakubo et al. | |
| 6,081,981 A | * 7/2000 | Demarest et al. | |
| 6,098,796 A | * 8/2000 | Januzeli et al. | ............ 206/63.3 |
| 6,105,339 A | * 8/2000 | Pohle et al. | |
| 6,135,272 A | * 10/2000 | Sobel et al. | ............... 206/63.3 |
| 6,138,053 A | * 10/2000 | Demarest et al. | |
| 6,205,748 B1 | * 3/2001 | Daniele et al. | ............... 53/430 |

FOREIGN PATENT DOCUMENTS

RU 424040 * 8/1999

* cited by examiner

*Primary Examiner*—Stephen F. Gerrity
(74) *Attorney, Agent, or Firm*—Emil Richard Skula

(57) ABSTRACT

A machine and process for packaging armed sutures into tray packages. The machine has a frame with a rotatable indexing disc member mounted to the top of frame. A plurality of tool nests are rotatably mounted to the top of the indexing disc. Tray packages mounted in the tool nests are rotated to wind sutures into a suture channel in the packages. A stylus having a front nose member and a rear heel member guides suture into the suture channel.

3 Claims, 23 Drawing Sheets

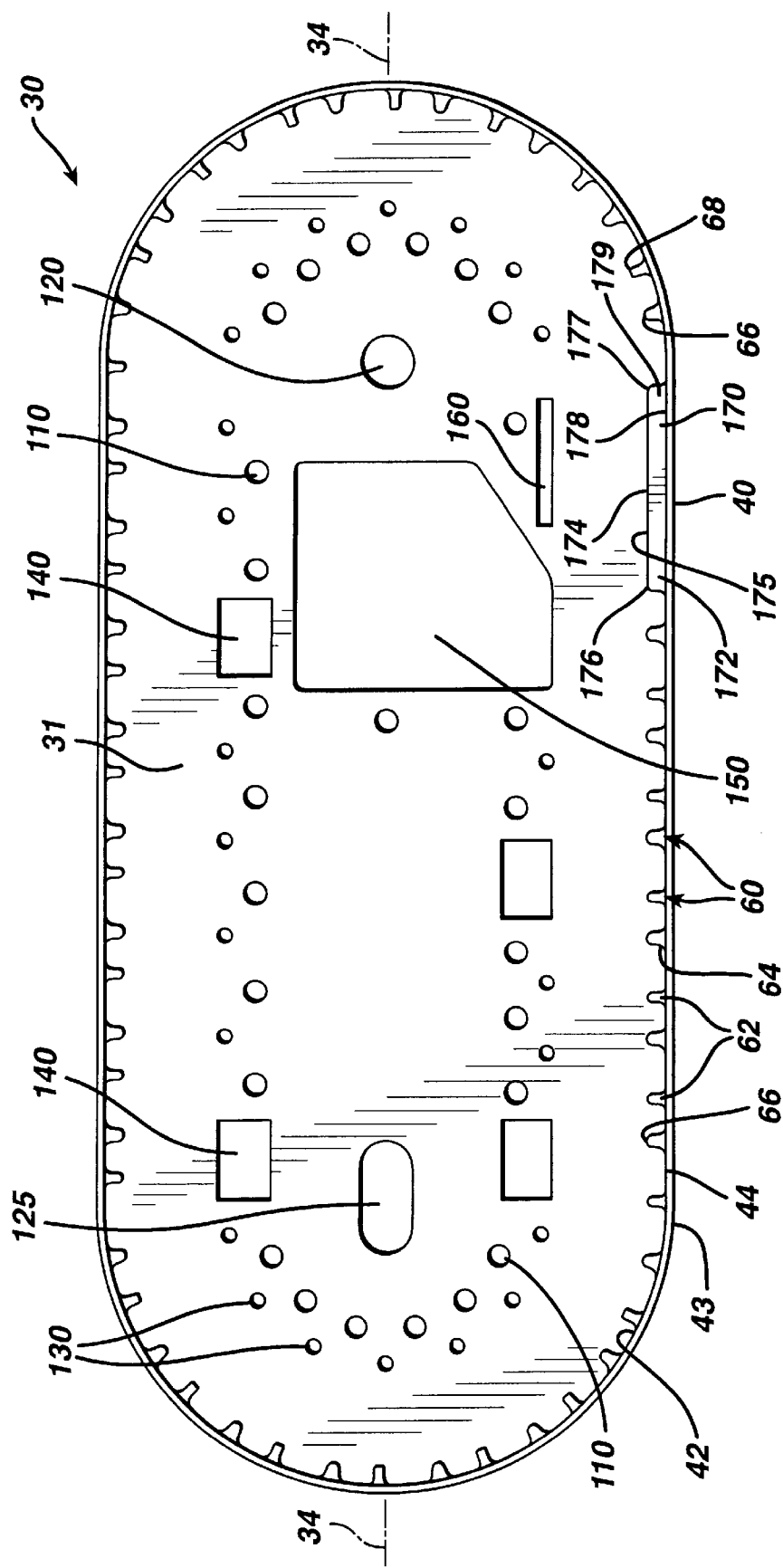

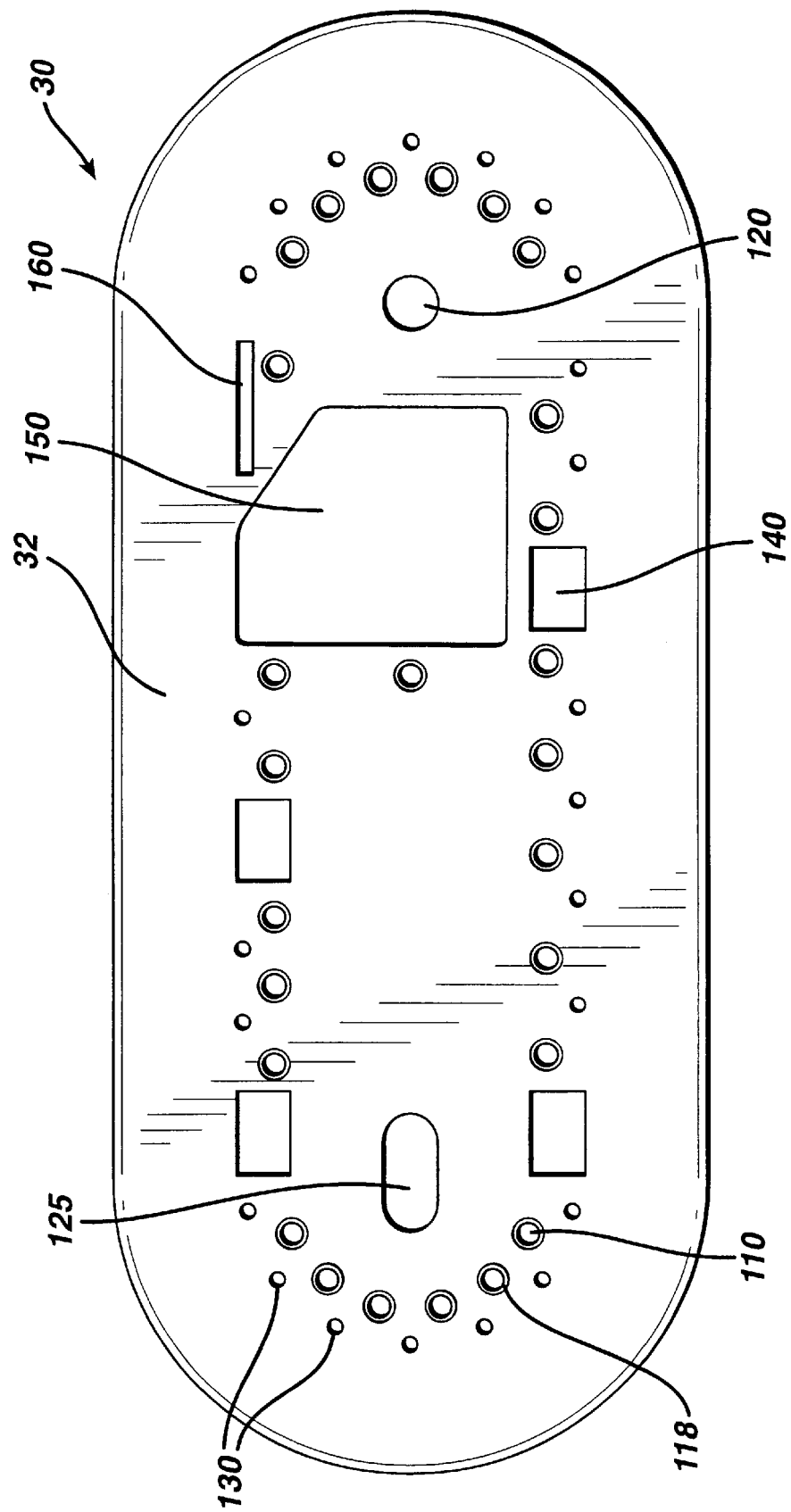

SUTURE WINDING MACHINE, SUTURE TRAY PACKAGE, AND METHOD OF WINDING SUTURES

TECHNICAL FIELD

The field of art to which this invention relates is packaging machinery, in particular, machinery for loading surgical sutures into packages.

BACKGROUND OF THE INVENTION

Surgical sutures having surgical needles attached to one or both ends are well known in the medical arts. Sutures having a single needle attached to one end are known as single-armed sutures. While sutures having needles attached to both ends are known as double-armed sutures. Sutures not having surgical needles mounted to an end are referred to as unarmed sutures. Double-armed sutures find particular utility in the following types of surgical procedures: cardiac valve replacement surgery, cardiac surgery, and bowel surgery.

In the past, surgical sutures were hand packaged into specially designed suture packages. Typically, the sutures were wound using conventional winding fixtures having winding pins. Although there may have been advantages associated with the hand winding methods of the prior art, one major disadvantage was that they were unnecessarily time consuming. In order to maintain high quality and to reduce costs, manufacturers of surgical sutures and surgical needles have developed high-speed packaging processes for packaging surgical needles and sutures into specially designed packages. Examples of packages which can be used in high speed winding applications are contained in U.S. Pat. Nos. 5,213,210, 5,236,083, 5,284,240, 6,098,796, and 6,135,272, the disclosures of which are incorporated by reference. High speed winding machines for packaging surgical sutures in such surgical suture packages are disclosed for example in U.S. Pat. Nos. 5,664,404 and 6,032,343 which are incorporated by reference.

Although the packaging machines and processes of the prior art are adequate for their intended use, there are certain types of surgical sutures which are particularly difficult to adapt to high speed winding or packaging machine operations. For example, suture for use in cardiac and cardiovascular surgical procedures is very delicate and any damage caused to the suture by handling or packaging can compromise the integrity of the sutures. In addition, it has been difficult to package such sutures in packages using high-speed automatic packaging machinery due in part to the fine gauge of the sutures. Also, it previously has not been possible to package double armed sutures in tray packages using high-speed winding equipment.

Accordingly, there is a need in this art for novel high-speed packaging machinery and processes for packaging surgical needles and sutures.

SUMMARY OF THE INVENTION

Therefore, it is an object of the present invention to provide novel, high-speed packaging machines for packaging surgical needles and sutures in tray packages.

Yet another object of the present invention is to provide such novel high-speed packaging machines having the capability of packaging single-armed, doubled-armed and unarmed surgical sutures.

It is yet another object of the present to provide novel processes for packaging surgical needles and sutures.

Accordingly, a high-speed suture packaging machine for packaging surgical needles and sutures in tray packages is disclosed. The machine has a frame having a top, a bottom, sides and an interior. A disc member or turret is rotatably mounted to the top of the frame, said disc member having a periphery, top, a bottom and a side about the periphery of the disc member. The disc member may be rotated or indexed to a plurality of index positions. A plurality of tool nests is mounted to the top of the disc. Each tool nest is rotatably mounted to the top of the disc member. The tool nests have a nest frame, having a top, a bottom and sides. At least two winding pin members extend up from the top of the nest frame. A rotatable tool mounted to the frame, said tool being displaceable downwardly to engage with the pin members on the nest frame, such that rotation of the tool will rotate the tool nest. A stylus member is movably mounted to the machine frame, for cooperation and engagement with the tool nests. The stylus comprises a frame having a top, sides and a bottom. A stylus is mounted to the bottom of the frame having a front nose member and a rear heel member separated by a suture opening. The stylus has a top surface. A door closing member extends down from the bottom of the frame adjacent to the stylus. A tray package mounted to the winding pins on place on top of the tool nest frame is rotated to wind sutures in a winding channel in the package.

Yet another aspect of the present invention is the combination of the afore-mentioned packaging machine and a suture tray package. The package has a flat base member having a top and an outer periphery. An outer wall extends up from the base member about the periphery of the base member. An inner wall, interior to the outer wall, extends up from the top of the base member. The inner wall having a top and said inner wall space away from the outer wall to form a suture channel. A plurality of doors extend from the top of the inner wall over the winding channel. At least two needle park members extend up from the top of the base member. The needle park members are located interior to the inner wall. Initially, the tray package is mounted on the winding pins to the top of the tool nest. A tray package is mounted to the top of a tool nest. Then the disc member is indexed to a suture loading station wherein both needles of a double armed suture are mounted into the needle parks of the tray package thereby forming a loop in the suture. Next, the tool nest is indexed to the machine winding station wherein the tool nest is engaged by a rotating tool, thereby rotating the tool nest and package and causing the suture loop to be wound in the suture channel.

Yet another aspect of the present invention is a method of winding a double-armed suture in a tray package using the afore-described packaging machine of the present invention. The method consists of providing the packaging machine of the present invention along with a tray package having a winding channel, and also providing a double armed suture.

These and other features, advantages and attributes of the present invention will become more apparent from the following description and accompanying drawings.

BRIEF DESCRIPTION OF THE DRAWINGS

FIG. 2b is a top view of a base member of the package of FIG. 2a

FIG. 2c is a bottom view of the base member of the package of FIG. 2a.

FIG. 2d is a bottom view of the channel cover member of the package of FIG. 2a.

DESCRIPTION OF THE PREFERRED EMBODIMENTS

A tray package 10 useful in the practice of the present invention is illustrated in FIGS. 2–7 and FIGS. 24–26. This package is also disclosed in U.S. Pat. No. 6,135,272, which is incorporated by reference.

Figure 1A:
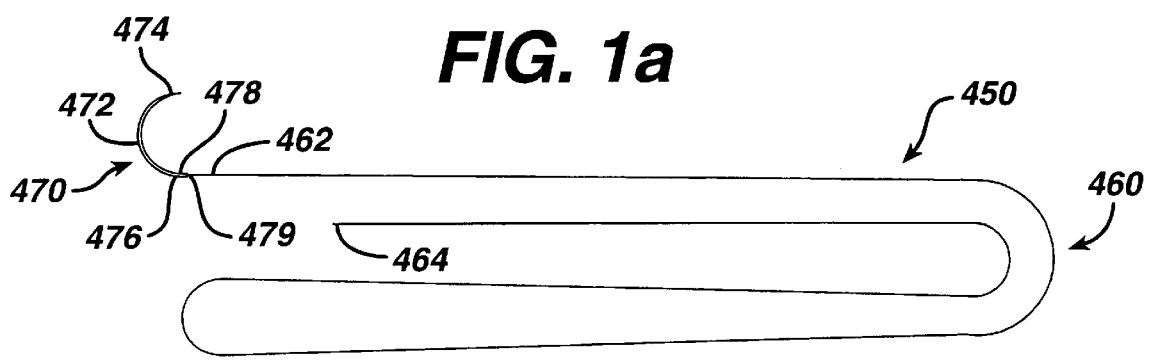
FIG. 1a is a plan view of a conventional single-armed suture which can be packaged using the packaging machines and processes of the present invention.
Figure 1B:
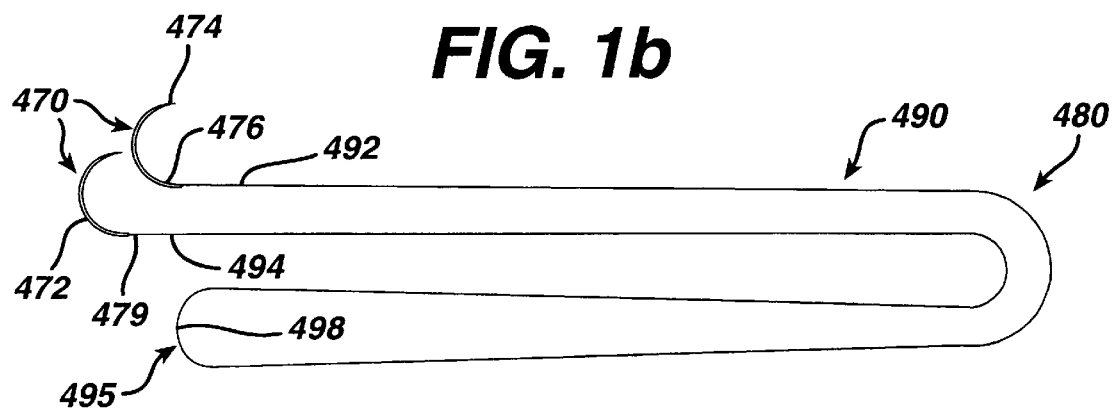
FIG. 1b is a plan view of a conventional double-armed suture which can be packaged using the packaging machines and processes of the present invention.
Figure 2A:
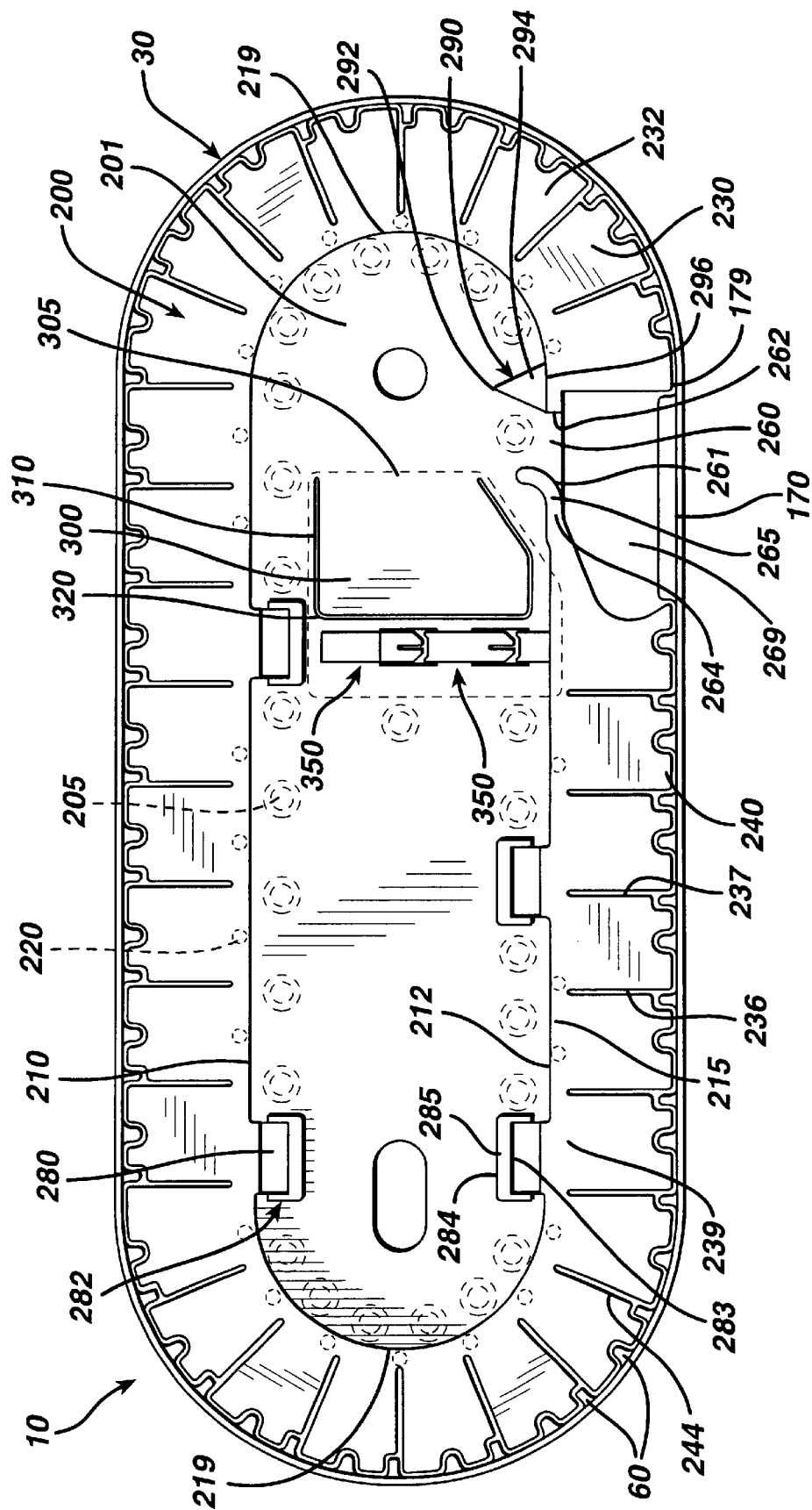
FIG. 2a is a top view illustrating a tray-type package particularly useful with the packaging machines and processes of the present invention, wherein the package has a winding channel for receiving suture, and needle parks for receiving needles; the package is an assembly of a lower base member and a top cover member having a plurality of cover door members.
Figure 2D:
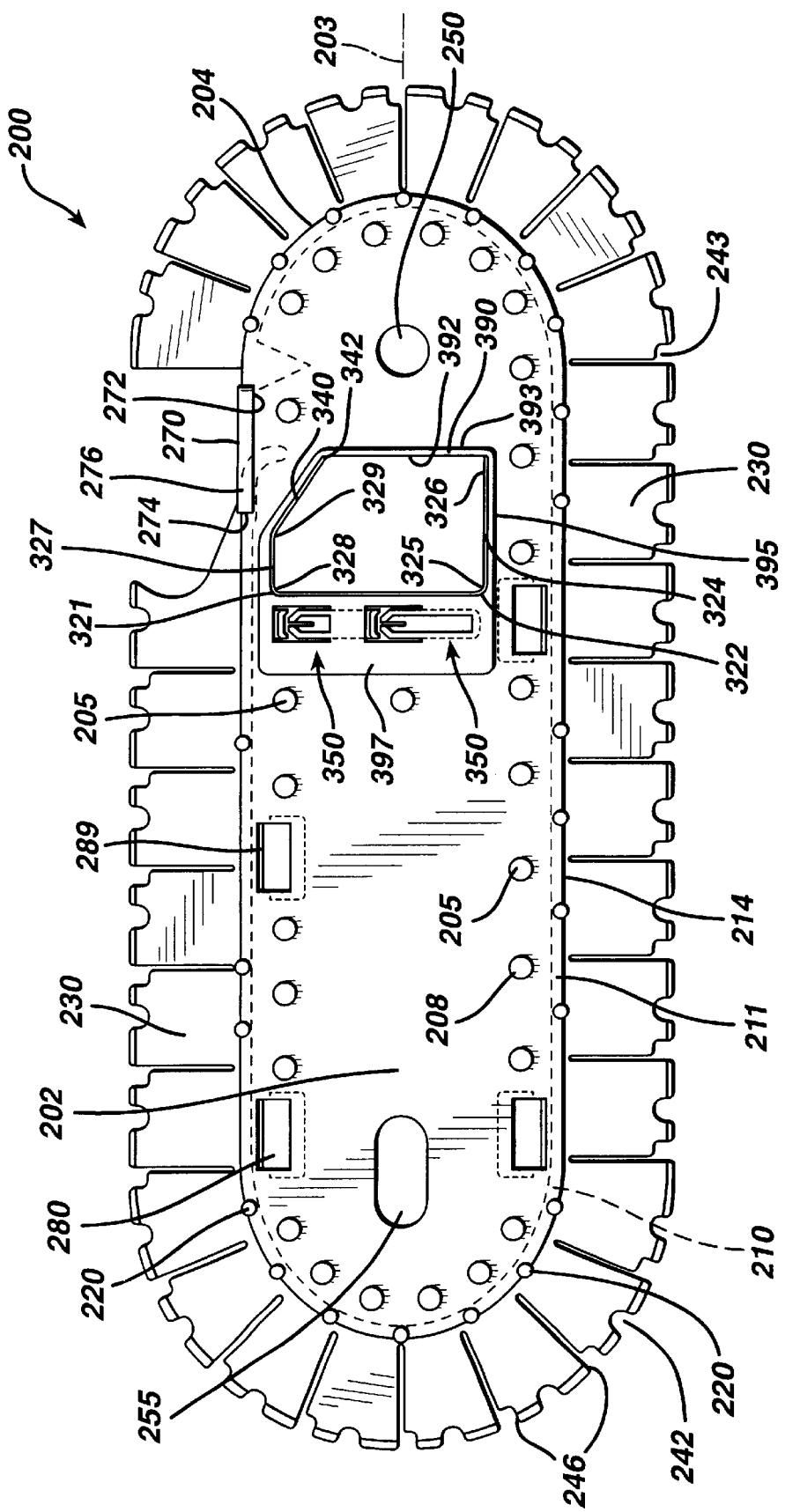
Figure 3:
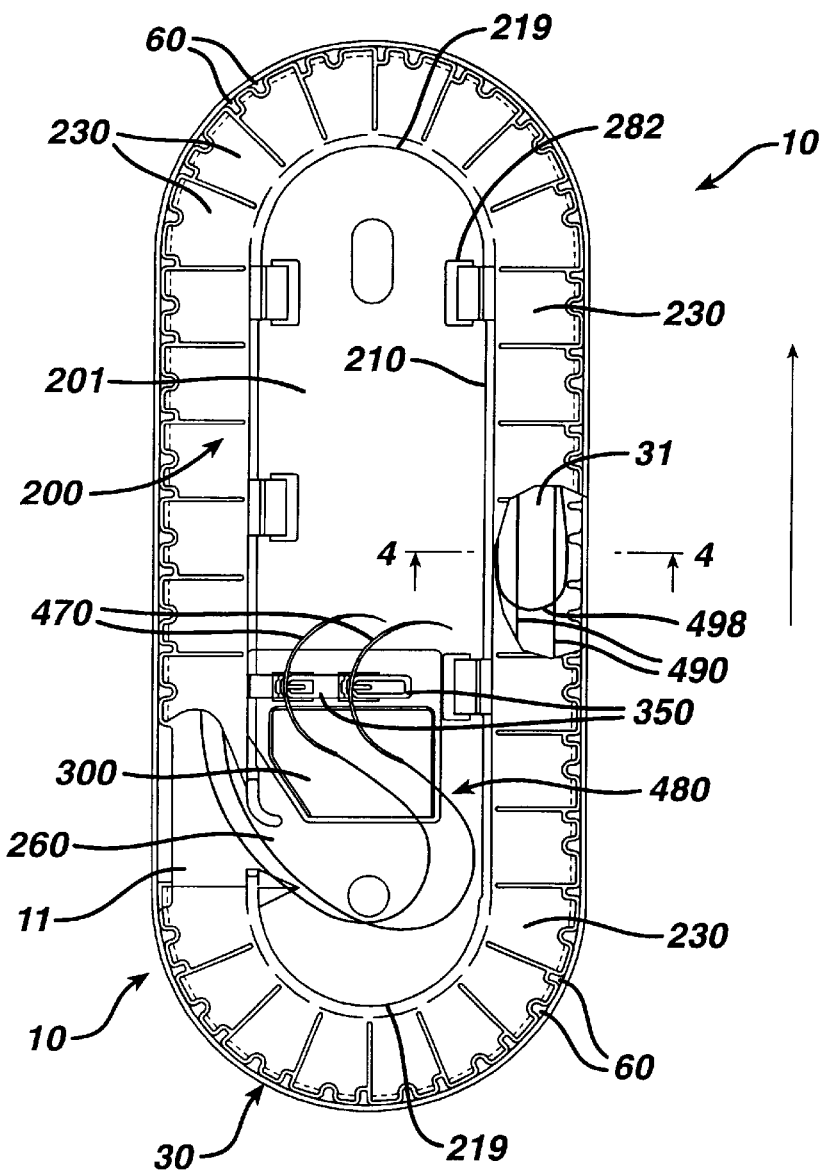
FIG. 3 is a top view of the package of FIG. 3, illustrating a double-armed suture wound in the winding channel, and having both needles mounted in needle parks.
Figure 4:
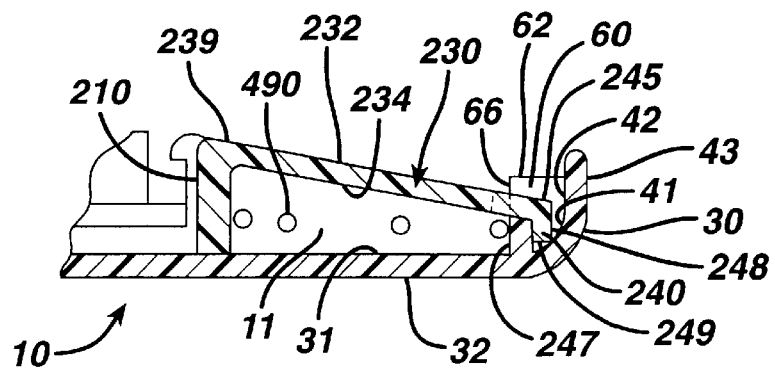
FIG. 4 is a partial cross-sectional view of the package of FIG. 3 taken along View Line 4—4, illustrating suture strands in the suture channel.
Figure 5:
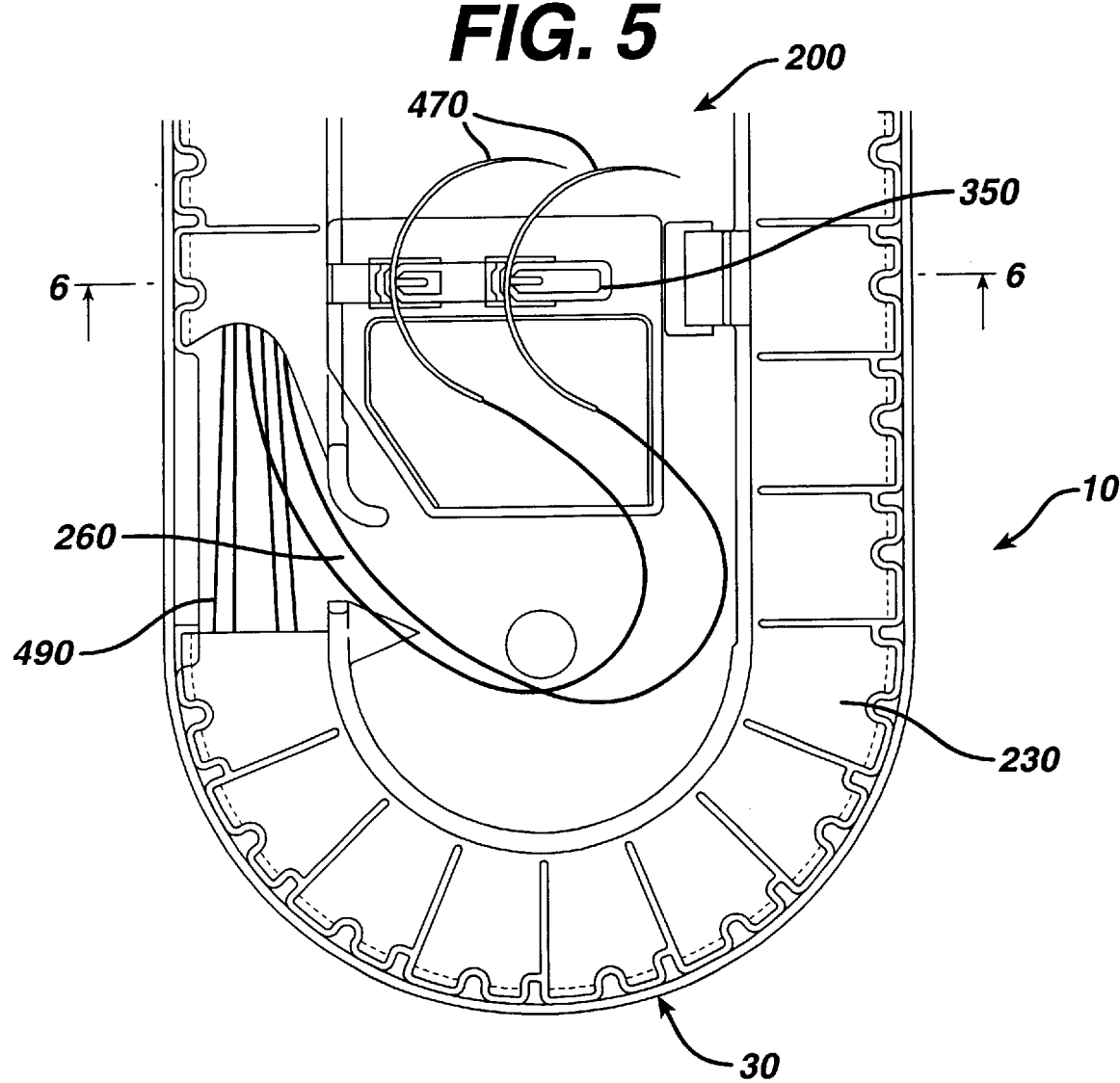
FIG. 5 is a partial, magnified top view of the package of FIG. 3 illustrating the distal ends of the suture adjacent to the needles exiting the suture winding channel.

The packaging machines and processes of the present invention are preferably used to package conventional surgical needles and sutures into suture tray packages having winding channels. Conventional surgical sutures typically have surgical needles mounted to one or both ends. Referring first to FIG. 1a, a conventional single-armed suture 450 is seen. The single-armed suture 450 is seen to have suture 460 having first and second opposed ends 462 and 464. Surgical needle 470 is seen to be a conventional curved surgical needle having curved member 472, a pointed distal end 474 and proximal mounting end 476. Contained in mounting end 476 is a conventional drilled mounting cavity 478, having opening 479. The end 462 of suture 450 is seen to be mounted in mounting cavity 478. Suture end 462 is inserted into opening 479 of mounting cavity 478 and then affixed or mounted in a conventional matter such as by mechanical swaging, gluing, ultrasonic welding, shrink tubing and the like. A conventional double-armed suture 480 is illustrated in FIG. 1b. The double-armed suture 480 is seen to have suture 490 having first and second opposed ends 492 and 494. The ends 492 and 494 are each seen to be mounted in the mounting cavity 478 of a surgical needle 470 to form double-armed suture 480. The suture ends 492 and 494 are mounted or affixed to needles 470 by inserting the needles through openings 479 and into mounting cavities 478, and then using conventional mounting processes as described above. The suture 490 of double-armed suture 480 is seen to have loop 495 in central section 496, having loop bottom 498, when the needles 470 are spatially located proximate to each other. Although not shown, conventional unarmed sutures do not have needles mounted to their ends.

The sutures and needles that can be packaged in the packages 10 using the machines and processes of the present invention include conventional surgical needles and conventional bioabsorbable and nonabsorbable surgical sutures and equivalents thereof. As mentioned previously, the conventional sutures may be conventional single-armed and double-armed sutures. Although not preferred, unarmed sutures may also be packaged using the processes and machinery of the present invention.

As seen in FIGS. 2–7, a tray package 10 useful in the packaging processes and with the packaging machines of the present invention is illustrated. The package 10 is seen to have base member 30, suture channel cover member 200, and optional top package cover 400. Referring now in more detail to FIGS. 2a–2d, the base member 30 is seen to have top side 31 and bottom side 32. Base member 30 is also seen to have outer periphery 35. The base member 30 is seen to be a substantially flat substantially oval shaped member having a longitudinal axis 34. However, although it is desired that the base member 30 along with the package 10 be oval shaped, other configurations can be used including circular, polygonal, square with rounded corners, and the like and combinations thereof and equivalents thereof. Extending upwardly about the periphery 35 of base member 30 is the outer wall 40. Outer wall 40 is seen to have bottom 41, inner side 42, outer side 43 and top 44. The standoff members 60 are seen to extend inwardly from the inner side 42 of the outer wall 40 onto the top side 31 of base member 30. Standoff members 60 are seen to have bottoms 64 and flat tops 62. The tops 62 of members 60 are preferably below the top 44 of wall 40. The standoff members 60 are seen to preferably have substantially curved outer end surfaces 66, and may also have flat outer end surfaces 68, or combinations of members 60 with flat and curved outer surfaces. If desired, the standoff members 60 may have other configurations for end surfaces including semi-circular, polygonal, oval, triangular, combinations thereof and equivalents thereof and the like.

Figure 6:
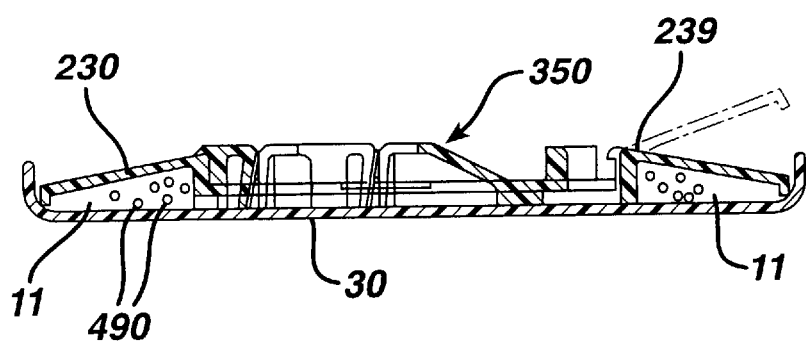
FIG. 6 is a cross-sectional view of the suture package of FIG. 3 taken along View Line 6—6 illustrating suture strands in the suture winding channel, and further illustrating one of the cantilevered cover door members moved to an open position.

Extending through the bottom of the base member 30 are a plurality of rivet retention holes 110. The rivet retention holes 110 are seen to be circular holes extending through the base member 30. It can be seen that on the bottom 32 of the base member 30, each rivet retention hole 110 is surrounded by an annular space 118 to facilitate spreading of the bottom of a rivet. Also extending through the base member 30, are the circular winding pin locating hole 120 and the oval pin locating hole 125. The holes 120 and 125 are seen to be disposed along longitudinal axis 34 and are at opposite ends of the base member 30. Also seen to extend through the base member 30 are the locating pin retention holes 130. Locating pin retention holes 130 are seen to be located between wall 40 and rivet holes 110. The holes 130 are preferably arrayed such that there is a pin hole between every two adjacent rivet holes 110 as seen in FIG. 6. The cover cleat retention holes 140 are also seen to extend through the base member 30. The holes are seen to be substantially rectangularly shaped, however, the holes may have any shape suitable for receiving the cleats on paper cover 400 as described herein below. The lifting tab receiving opening 150 is seen to be located in base member 30 toward circular locating hole 120. Also extending through base member 30 adjacent to opening 150 is the rectangular opening 160 for receiving suture port tab member 290. Extending inwardly from the inner side 42 of outer wall 40 and up from top side 31 is the suture port wall 170 having top 172, bottom 174 and inner surface 175, and ends 176 and 177. Adjacent to end 177 is notch 178 creating support surface 179. Inner surface 175 may be flat or curved or have other geometric shapes and combinations thereof.

Referring now to FIGS. 2a, 2d, and 3–7, the suture channel cover 200 is seen to be illustrated. The suture channel cover 200 has top side 201, bottom side 202, and periphery 204. Cover 200 is also seen to have longitudinal axis 203. Extending downwardly from the bottom 202 of the channel cover member 200 are the rivets 205. Rivets 205 are seen to have sides 206 and bottoms 208. The rivets 205 are preferably circular in cross-section, but may have other geometrical cross-sections including oval, square, polygonal, and the like and equivalents thereof. Although not preferred, rivets 205 may be replaced by other conventional fastening devices including locking pins, screws, etc. The holes 110 would be changed accordingly to adapt to any such different fasteners. Also extending downwardly from bottom 202 are the locating pins 220. Locating pins 220 are seen to have bottoms 228 and sides 226. Pins 220 preferably have a cylindrical configuration but may have other geometric shapes as well. Also seen to extend upwardly from the top 201 of the cover 200 about the periphery 204 is the peripheral track wall 210. Track wall 210 is seen to have inner side 212, outer side 214, bottom 211 and top 215 and opposed ends 219. It is preferred that the sides 226 of pins 220 extend partially out from outer side 214 on the opposed curved end sections of track wall 200. optionally, the sides 226 of pins 220 may extend partially out from the inners side of track wall 210 adjacent to ends 219.

Extending outwardly from the track wall 210 are the cover door members 230. It is preferred that the cover door members 230 extend out from the top 215 of wall 210, but may also extend from the side 214. The cover door members 230 are seen to have tops 232, bottoms 234, opposed sides 236 and 237, outer free ends 240 and hinged ends 239. Preferably, the hinged end 239 has a "living hinge" configuration wherein the door is cantilevered. The cover door members 230 are angulated with respect to inner track wall 210 such that the ends 240 of the door members 230 are located in the resting state below the bottom 202 of the cover 200 prior to assembly of package 10. Each cover member is seen to be separated by a space 244. The cover members are further seen to have an outer end 240, a central notch 242 and an offset notch 243 adjacent to one side. The central notch 242 is seen to be semi-circular in shape although other geometric configurations can be used. The notch 243 is seen to extend into outer end 240 and the outer end of the side 237. Notch 243 is seen to be a substantially rectangularly shaped opening having curved corners, although other geometric configurations may be used. Extending downward from the end 240 of cover member 230, is the downward rim 245. Downward rim 245 is seen to have inner side 247, outer side 248 and bottom 249 and ends 246. As mentioned above, although it is preferred that hinged ends 239 extend from track wall 210 in a manner to form a "living hinge", cover members 230 may also be connected or mounted to wall 210 using other conventional hinges and attachment methods.

The pin winding holes 250 and 255 are seen to be contained at opposite ends of the cover member 200. Winding pin holes 250 and 255 are seen to extend through member 200 and to be disposed in cover member 200 along longitudinal axis 203, toward either end, and are further seen to line up with winding holes 120 and 125 in base member 30. Winding pin hole 250 is seen to be circular in shape, while winding pin hole 255 is seen to be oval. However, other geometric shapes can be utilized. The suture exit port 260 is seen to be contained in track wall 210. Exit port 260 is seen to have ends 261 and 262. Adjacent to port 260 is the track opening 269. The curved arm 264 having inwardly curved end 265 is seen to extend up from top side 201 beginning at inner wall 210 adjacent to end 261 of port 260. Extending downward from the bottom side 202 of cover member 200 next to the port 260 is the port tab member 270. Tab member 270 is seen to have opposed longitudinal sides 272, opposed ends 274, and bottom 276. Tab member 270 is in alignment with rectangular port tab opening 160 in base member 130. Also seen to extend through the cover member 200 are the cover tab mounting holes 280. Each tab mounting hole 280 is seen to be surrounded on three sides by wall 282 extending up from side 201 of cover 200. Wall 280 is seen to have inner side 283, outer side 284 and top 285. Cleat member 289 is seen to extend down from the bottom 202 of member 200, adjacent to opening 280 and beneath track wall 210. Adjacent to end 262 of the port 260 and extending up from top side 202 is ramp member 290. Ramp member 290 is seen to preferably have a conically shaped configuration with apex 292 and curved top surface 294 and end 296, however other ramp configurations may be utilized. The lifting tab 300 is seen to be formed in base member 30 by the slit 310. Slit 310 is seen to have section 320 which is substantially perpendicular to the longitudinal axis 203 of cover member 200. Slit section 320 is seen to have ends 321 and 322. Intersecting section 320 at ends 321 and 322, respectively, and perpendicular thereto, are the side slit sections 324 and 327 having ends 325 and 326, and ends 328 and 329, respectively. Intersecting the end 329 of slit 327 is the angulated slit 340 having end 342. Between the ends 342 of slot 340 and end 326 of slot 324 is the living hinge member 305. Living hinge member 305 permits the lifting tab 300 to rotate about the hinge 305 and down into opening 150 in base member 30. An equivalent conventional hinge can be used in place of a living hinge, although not preferred, and other conventional ways of mounting the tab 300 to cover member 200 may also be utilized. Adjacent to the tab 300 are the needle park members 350. Members 350 are seen to have hinged arms 351 having first end 352 fixed to top 201 of cover member 200 and having opposite free end 353, which is divided by slot 354. Arm 351 can deflect or rotate about fixed end 352 into opening 360. The free end 352 is seen to be angulated from a top perspective to an edge 356. Each member 350 is seen to have cavity 358. Extending through member 200 below each free end 353 are the park openings 360. Adjacent to each free end 353 of the park members 350 are the cantilevered retention arms 370. The retention arms 370 are "L-shaped" members having smaller fixed legs 372 and longer movable legs 374. Movable legs 374 have ends 375 which may extend into park openings 360. Free ends 353 and legs 374 are separated by spaces 379. Extending downward from bottom 202 of member 200 about the periphery of slit 310 and also about openings 360 is the spacer wall 390 having inner side 392, outer side 393 and bottom 395. The spacer wall has thicker section 397 adjacent to openings 360.

The previously described package 10 are preferably assembled in the following manner. Base member 30 is aligned with cover member 200 such that the rivets 205 are in alignment with the rivet receiving holes 110, and locating pins 220 are in alignment with openings 130. Also, winding pin openings 255 and 250 are aligned with openings 125 and 120 respectively. Then, cover 200 is mounted to base member 30 such that the rivets 205 are inserted into and through the holes 110 and locating pins 220 are inserted through holes 130, and tab 290 is contained within opening 160. When this is accomplished, the standoff members 60 are contained within the notches 242 and 243 of door members 230. In addition, the spacer wall 390 is contained within opening 150. Then, the ends 208 of the rivets 205 are spread by using conventional techniques such as heating, ultrasonic treatments, and the like such that the cover 200 is firmly affixed to the base member 30, and the riveted or spread ends 208 are contained within annular openings 118. At this stage, the bottom 202 of cover member 200 is substantially in contact with the top 31 of the base member. When package 10 is thusly assembled, a suture channel 11 is formed consisting of the inner sides 247 of the rims 245 of the cover door members 230, the surfaces 66 and 68 of the standoff members 60, the top side 31 of member 30, and the outer side 214 of track wall 210. The channel 11 is covered by the cover members 230. When assembled, the bottoms 249 of cleats 245 are seen to be resting at least in part on top 31 of member 30, and the bottom 249 typically has at least some downward bias against top side 31 provided by cover door member 230.

The tray packages, such as package 10, useful with the packaging machinery and in the processes of the present invention may be manufactured from conventional moldable materials. It is especially preferred to use polyolefin materials such as polyethylene and polypropylene, other thermoplastic materials, and polyester materials such as nylon, and equivalents thereof. Preferably, the packages are injection molded, however, the packages may be formed by other conventional processes and equivalents thereof including thermo-forming. If desired, the packages may be manufactured as individual assemblies or components which are then assembled.

Although it is preferred to use a tray package 10 in the processes and with the package machines of the present invention, other conventional tray packages, and equivalents thereof, having suture channels may also be utilized.

Figure 8:
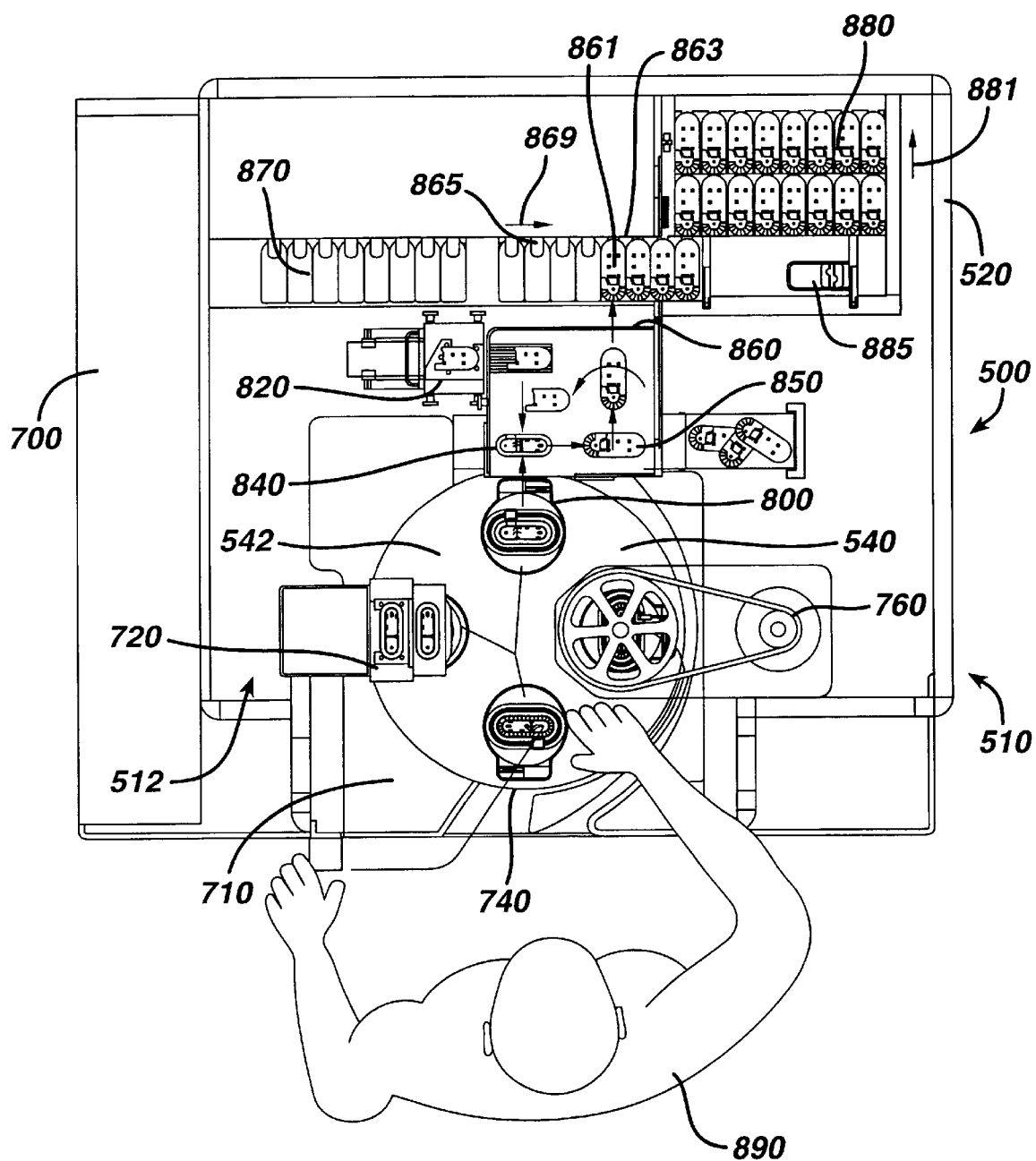
FIG. 8 is a plan view of a packaging machine of the present invention having partial manual operation; also illustrated, diagrammatically, is an operator.

A preferred embodiment of a packaging machine 500 the present invention is seen in FIG. 8. The zipper package assembly machine 500 is seen to be a rotary index-type machine combined with linear slides to transport a tray package, such as package 10, through its assembly sequence. The machine has a frame 510 having a top 512, a bottom 514 and sides 516; and frame 510 also has interior 518. Machine 500 is further seen to have machine enclosure 520 surrounding the sides 516 of the machine frame 510. A main rotary indexing disc-shaped turret 540 is seen to be rotatably mounted to the top 512 of frame 510. The circular turret 540 is seen to have top 542, bottom 544 and side 546. The turret 540 is rotatably mounted to the top 512 of frame 510 in a conventional manner by using a shaft and a bearing. The turret 540 is rotatably indexed in a conventional manner by using a conventional indexing motor assembly mounted in the interior 518 of frame 510 which drives a belt, which in turn engages gear teeth about the side 546 of turret 540. Mounted to the top 542 of turret 540 are a plurality of tool nests 600. Also mounted to the frame 510 is a conventional electronic controls enclosure 700 containing conventional electrical/electronic controls for controlling machine 500 and its individual work stations, e.g. conventional program logic controllers, computers, etc. It is seen that additionally mounted to the top 512 of frame 510 is a machine top tool plate 710 with feeding and assembly stations positioned and fixedly attached thereto.

Mounted adjacent to the turret 540 are the molded tray hopper and feeding station 720, the suture load station 740, the suture winding station 760, the package transfer station 800, the lid hopper and feeding station 820, the lid assembly station 840, the accept/reject station 850, the magazine load station 860, the empty magazine feed station 870, and the completed product magazine discharge station 880. Feeding armed sutures 450 or 480 to the machine 500 can be done manually by using an operator 890 at load station 740 as illustrated, or can be done in a conventional manner automatically, for example by using a conventional robot or other device (not shown).

Figure 9:
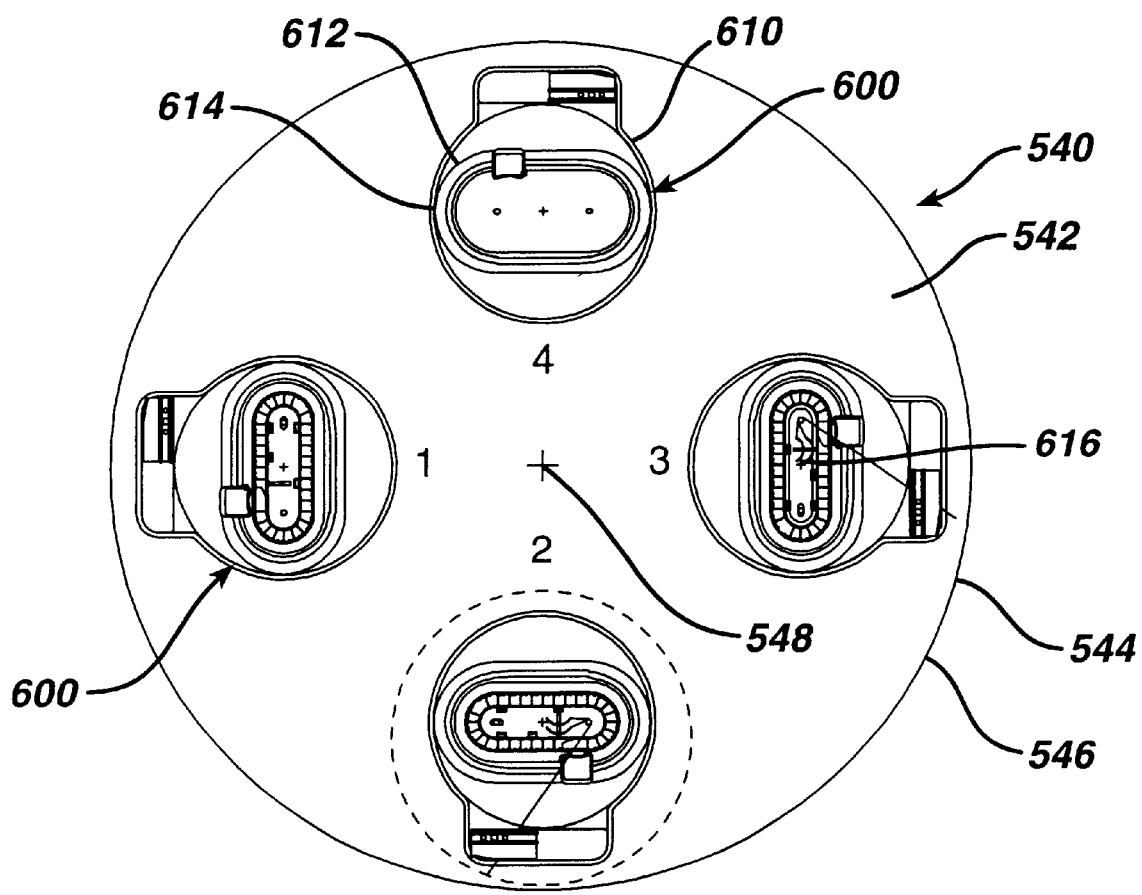
FIG. 9 is an illustration of the machine turret of the machine of FIG. 8 having four tool nests mounted thereon.

FIG. 9 illustrates an isolated top view of the indexing turret 540. A plurality of identical tool nests 600 are rotatably mounted, and preferably equally spaced, to the top side 542 about the periphery of turret 540. The turret 540 is rotatably mounted to frame 510 about a vertical turret axis 548. Turret 540 is driven by a conventional indexing motor, belt drive and gear teeth arrangement. The turret 540, having four of the previously mentioned tool nests 600 in the preferred embodiment, indexes 90° during each machine cycle to each of the previously mentioned machine stations. Each tool nest 600 is itself rotatably mounted to turret 540 by the use of bearings and shafts.

Figure 10:
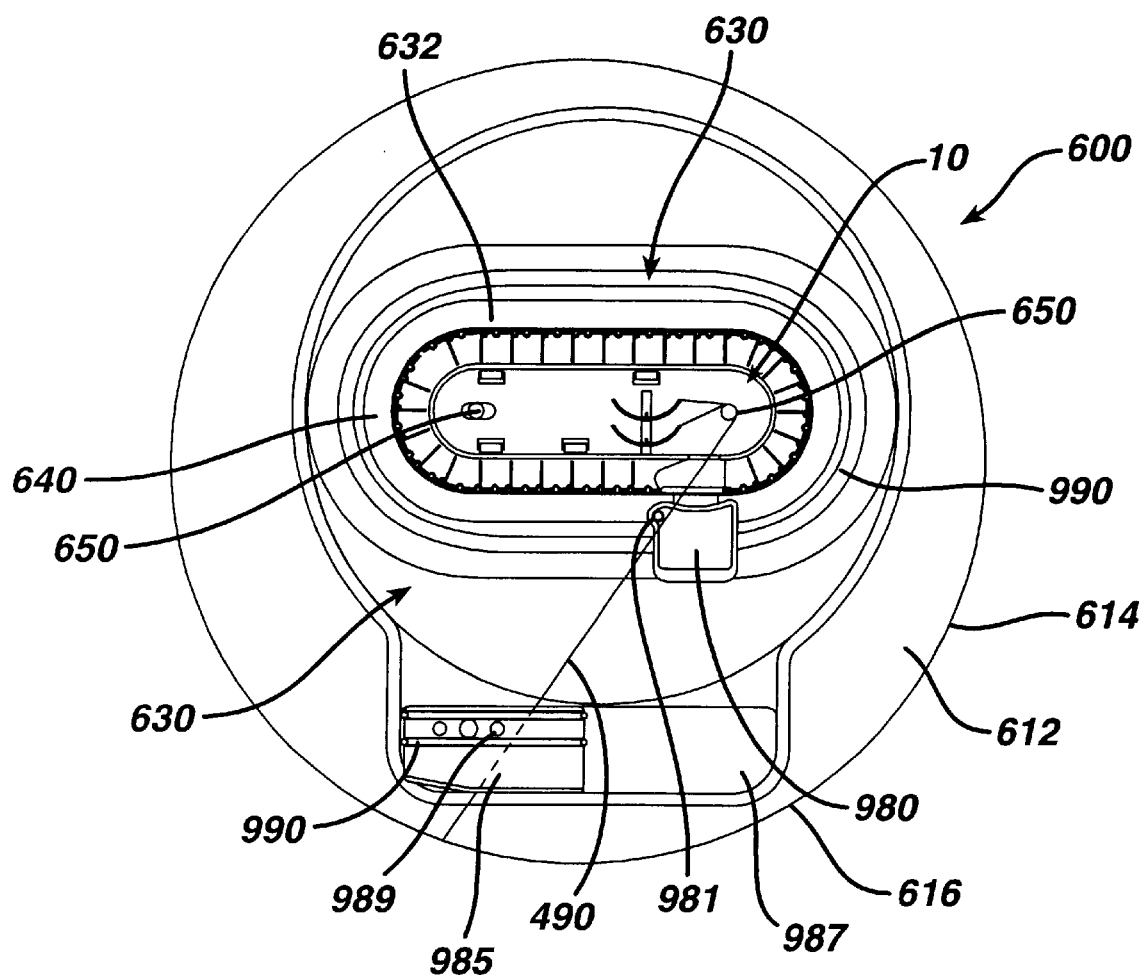
FIG. 10 is an enlarged illustration of a tool nest of the machine turret of FIG. 9, illustrating a suture being wound into the winding channel of a package.
Figure 14:
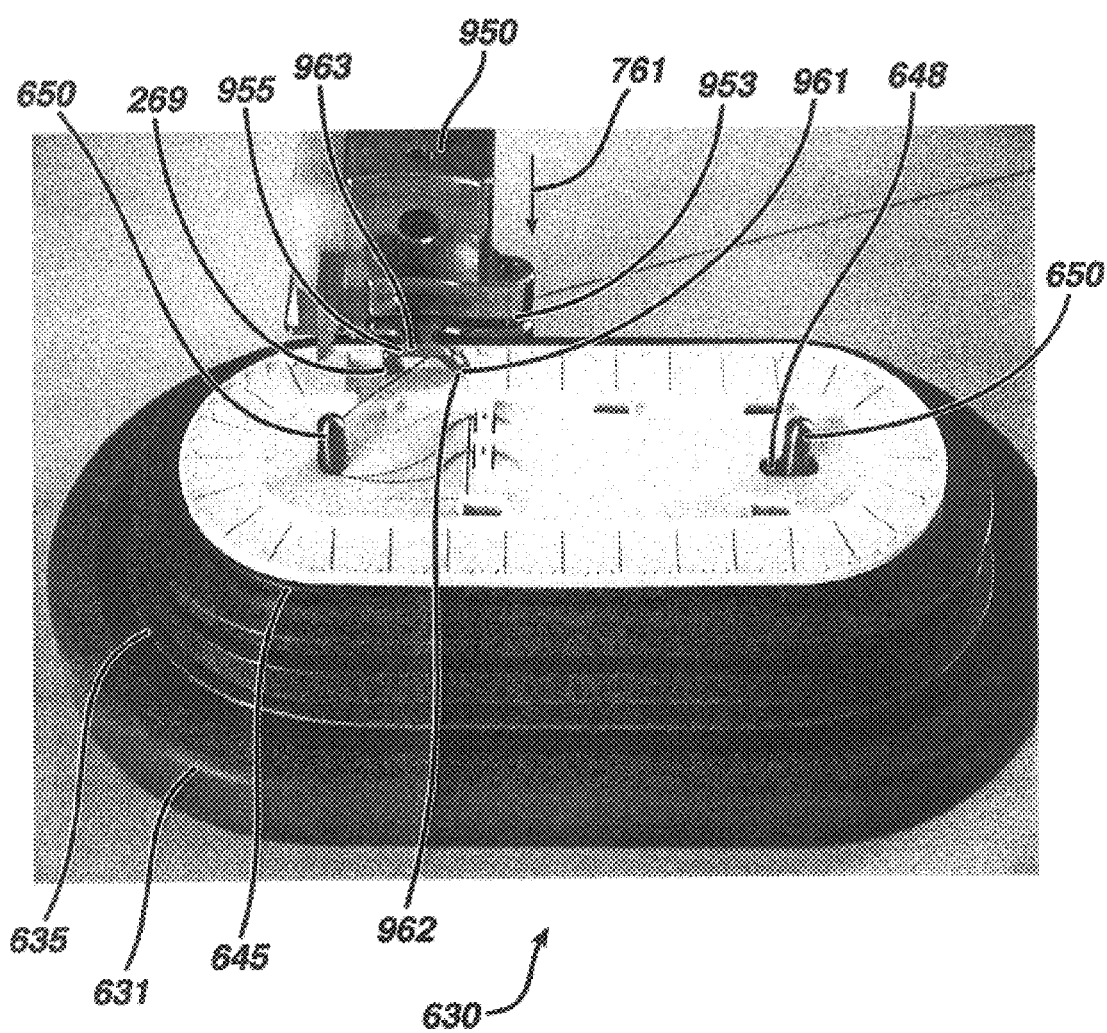
FIG. 14 is a photograph illustrating the stylus assembly of FIG. 13 inserted into a suture channel of a tray package adjacent to the channel opening, after needles have been placed in the needle park and prior to winding the suture into the suture channel; the tray package is mounted in a tool nest.

Referring to FIGS. 10 and 14, the tool nests 600 are seen to have a stationary frame 610 having a top 612, a bottom 614 and side 616. Extending upward from the top 612 and rotatably mounted to frame 610 and turret 540 is the tray engaging member 630. Engaging member 630 is seen to have bottom 631, top 632, stepped sides 635 and central flat top 640 surrounded by upwardly extending wall 645. The top 640 and wall 645 form receiving platform 648 for tray packages such as package 10, in order to maintain the packages in place during the various machine cycles. The winding pins 650 are seen to extend up from top 640.

Figure 11:
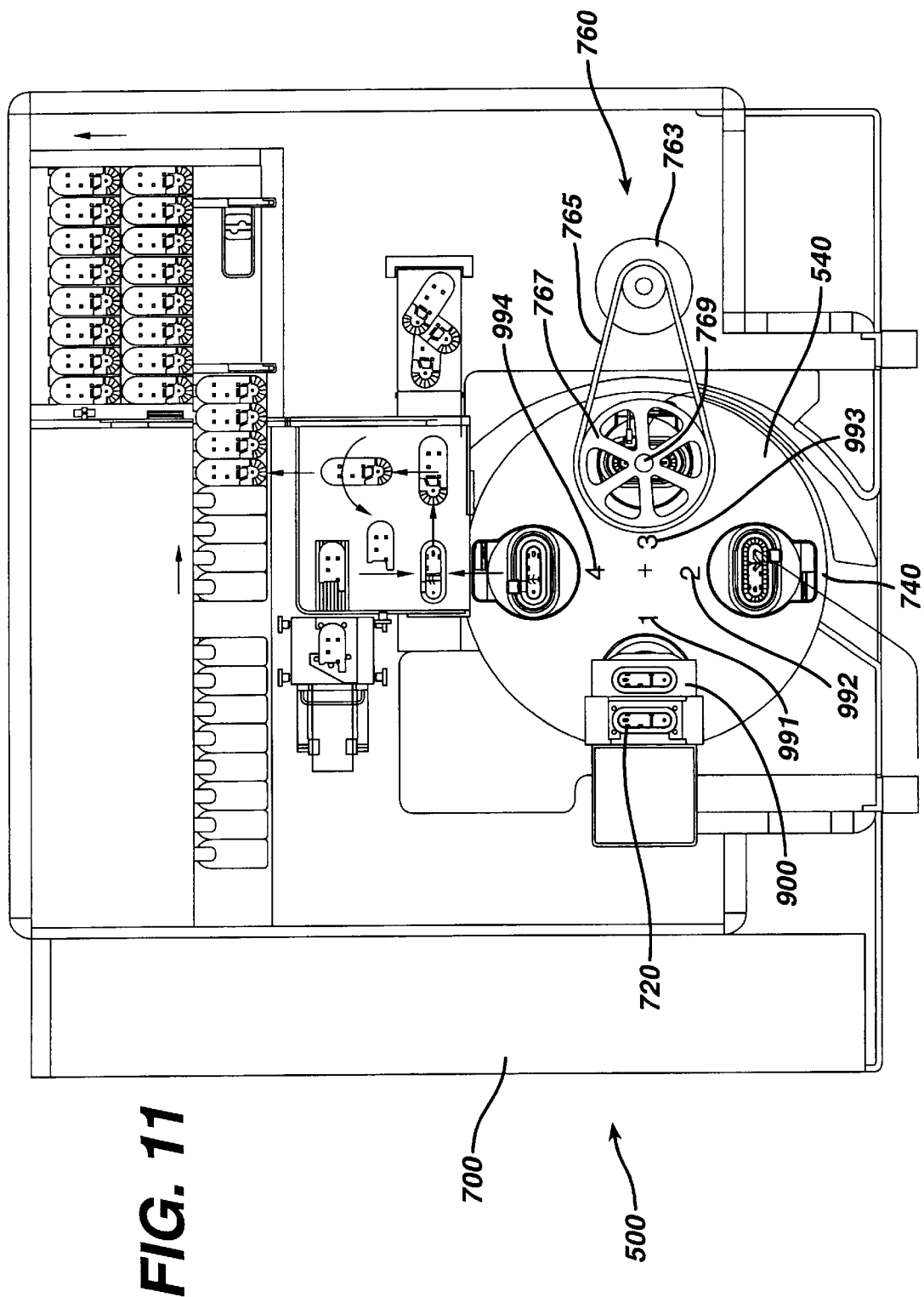
FIG. 11 is a magnified view of the machine top of FIG. 8 illustrating the process flow of the packaging operation.

Referring now to FIG. 11, the machine sequence for packaging a double-armed suture 480 in a package 10 using a machine 500 of the present invention is illustrated. Initially, at machine index station 991, where the molded tray hopper and feeding station 720 is mounted, an empty package 10 is loaded from a vertical stacking magazine 900 with a shuttle slide (not shown) onto a platform 648 of nest 600 such that the pins 650 are engaged in the winding pin openings 120, 125, 250 and 255. The vertical stack of packages 10 is contained by a plurality of fixed vertical rods that confine the tray packages by contacting their outer edges, allowing said packages to descend by gravity, being fed from the bottom of the stack by a slice type shuttle as the machine is cycled. The feeding mechanism (not shown) places the empty molded tray 10 onto platform 648 and onto winding pins 650 of tray engaging member 630 of nest 600 as seen in FIG. 10, so that corresponding pin receiving holes 120, 125, 250 and 255 in the package 10 are coincident with said pins 650.

After a package 10 has been loaded into a nest 600, the machine is indexed (i.e., rotated) 90 degrees from machine index station 991 to machine index station 992, where needle and suture loading station 740 is located. Armed sutures, such as double-armed sutures 480 are partially loaded into packages 10 at station 740, as illustrated in FIG. 9, either manually or automatically, as described below by initially loading needles 470 into needle park members 350 of package 10 such that the needles 470 are securely mounted in the park members 350. FIG. 10 is an enlarged view of a tooling nest 600 of FIG. 9, illustrating a package tray 10 at machine station 992 (needle and suture loading station 740) after the needles 470 of the double-armed suture 480 have been placed into needle park members 350 of package 10 with suture loop 495 extending out through exit port 260 in wall 210, and threaded through and engaged by stylus insertion tool 955. As illustrated, needles 470 are have been pressed downwardly into needle parks 350, and the suture strands 490 of loop 495 are guided about winding pin 650 as shown, over the winding stylus base 980, against base pin 981, and under friction hold down 985. Hold down weight block 985 exerts a gravitational force against a corresponding platform 987 through resilient elastic bands 990 stretched therearound, thereby frictionally fixing the position of suture strands 490 therebetween. Elastic bands 990 are preferably manufactured of soft, rubber-like material, to prevent damage to the suture strands, but may be manufactured from equivalent conventional materials and devices which provide and equivalent biasing force. The stylus base pin 981, the hold down vertical shaft 989, and the winding pin 650 are configured to locate the suture strands 490 through the gap 260 in the tray inner wall 210 and generally within the stylus access opening 269 in the tray suture channel 11. The trailing end or loop 495 of the suture 490 beyond the hold down 985 hangs freely.

The winding operation commences after the turret 540 indexes 90° counter clockwise, thereby moving the package 10 with double-armed suture 480 loaded at machine index station 992 to machine index station 993 as seen in FIG. 11. Located at machine index station 993 is the suture winding station 760. The freely hanging suture loop 495 is pulled along by the index rotation of the turret 540, guided by a fixedly mounted trough that is fabricated with a smooth surface that prevents damage to suture loop 495.

Referring to FIG. 9, the tooling nests 600 are seen on turret 540. Each of the four tooling nests 600 are rotatably mounted to turret 540, and are rotatable about their individual vertical axes, for example axis 616 for nest 600 at machine station 993, after a mechanical latch within the turret mechanisms (not shown) is released. Referring next to FIG. 10, winding stylus base 980 is free to slide parallel to the outer periphery 35 of the package tray 10, guided by cam tracks 990 in the tooling base 600 after being similarly mechanically unlatched.

Figure 12:
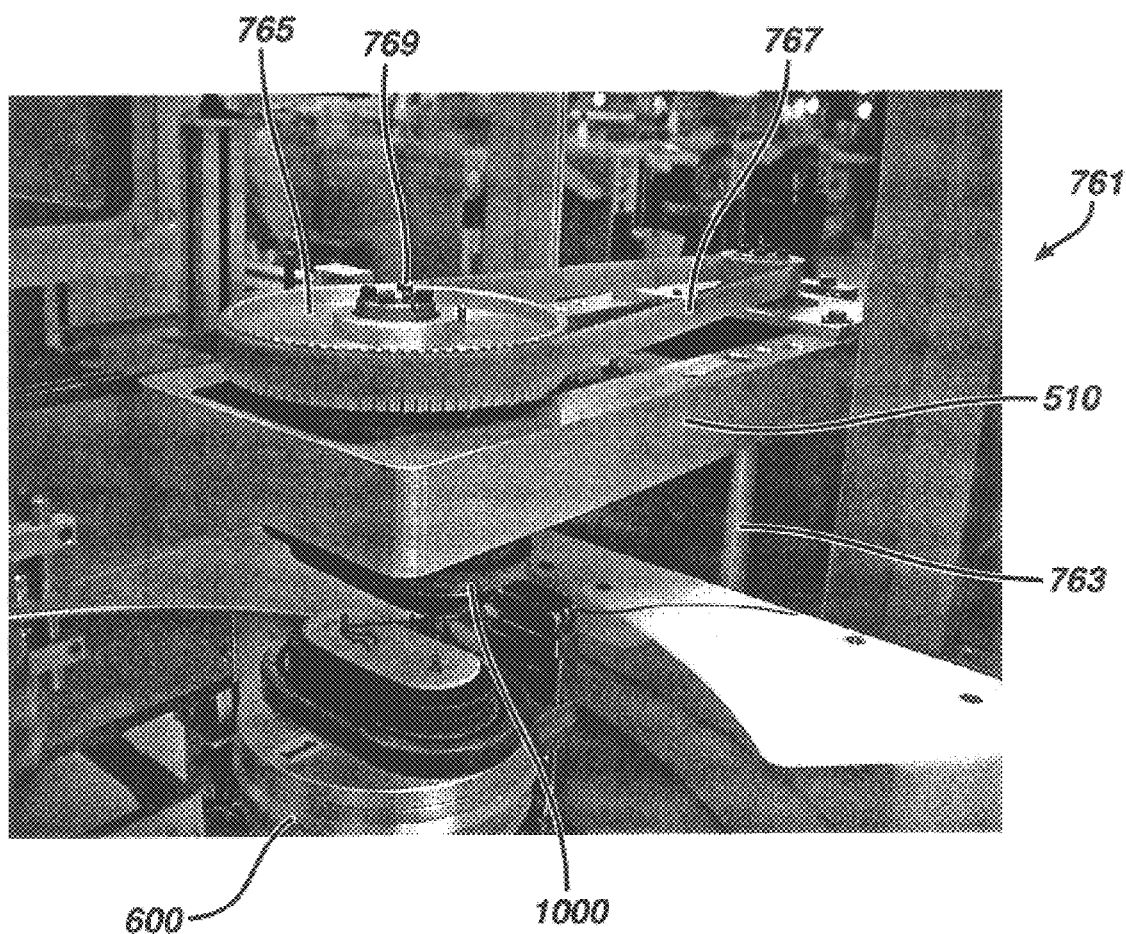
FIG. 12 is a photograph illustrating the machine winding drive station used for driving a tool nest of the packaging machines of the present invention.

FIGS. 11 and 12 illustrate the winding station power drive assembly 761 at winding station 760. Assembly 761 consists of a servo motor 763, toothed drive belt 765, and driven sprocket 767. A vertical shaft 769 is located by appropriate bearings (not shown), rotatably mounted to the machine frame 510 and coaxial with the rotation axis 616 (FIG. 9) of the tool nest 600 therebelow.

Turret 540 is shown in machine index position 993 with indexing tool nest 600 containing a package tray 10 with needles 470 of double-armed suture 480 assembled thereto, before the suture winding operation commences.

An upper tooling assembly 1000 rotatingly fixed to the vertical shaft 769, but vertically slideable on splines thereon, is vertically displaced downward and engaged with the lower tooling 600 therebelow. This downward vertical displacement causes pins 650 in the lower tooling nest 600 to engage mating holes (not shown) in the upper tooling 1000, thereby causing the driven rotation of the upper tooling 1000 by the belt 767 and sprocket 765 to likewise drive rotation of the lower tooling nest 600 about vertical axis 616 (see FIG. 9) being torsionally integral therewith. A winding stylus assembly 950, described hereinbelow, is similarly engaged with the stylus base 980 (FIG. 10) by meshing pins and mating holes therein (not shown). The suture friction hold down 985 is mechanically raised, minimally to prevent suture twisting, to remove frictional drag forces on the suture during the winding operation.

Figure 13:
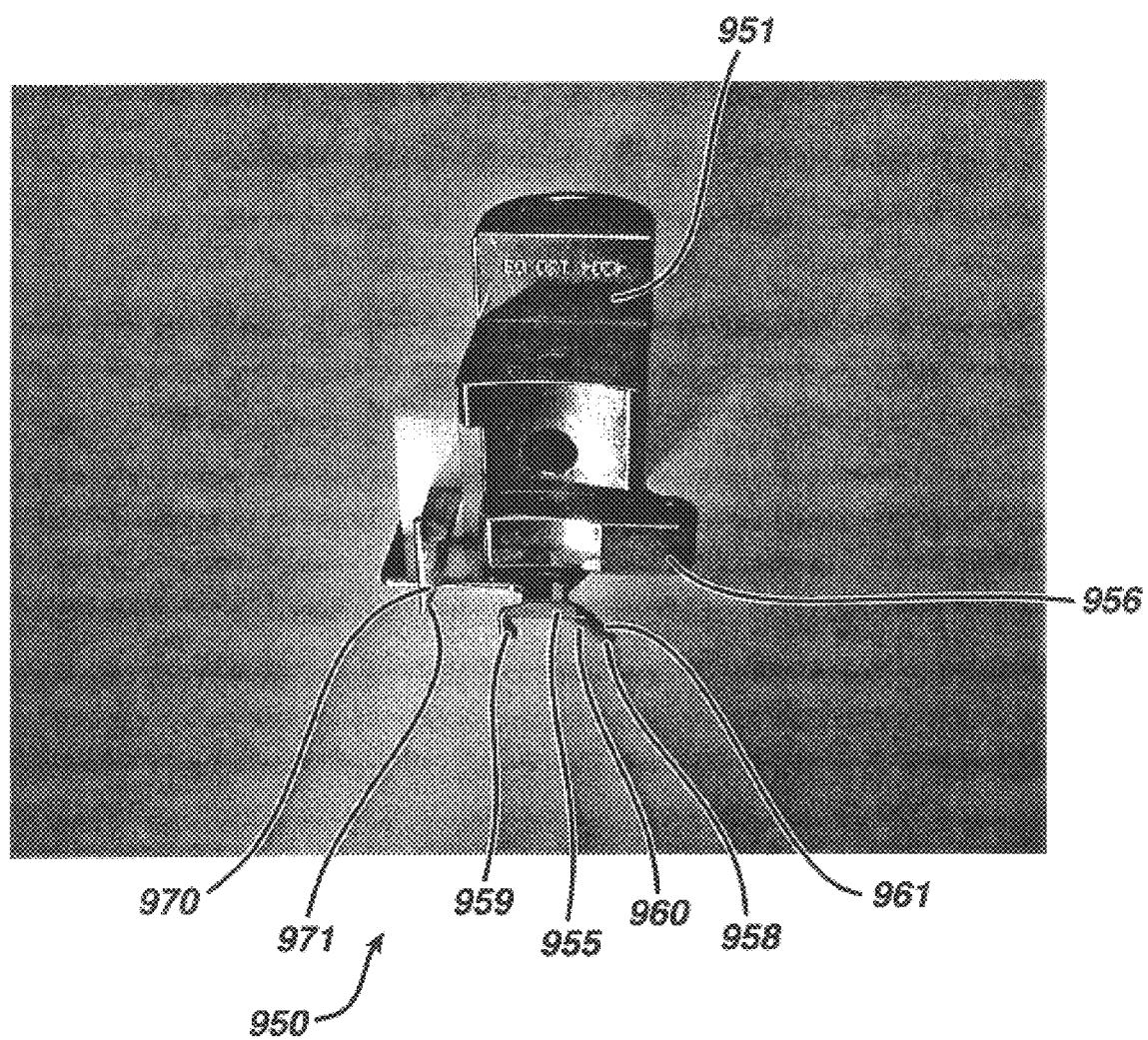
FIG. 13 is a photograph illustrating a winding stylus assembly used at a winding drive station to emplace suture in a suture winding channel.

The winding stylus assembly 950, illustrated in FIG. 13, has a frame 951. Extending down from the bottom 952 of frame 951 is a stylus insertion tool 955, a flap closing tool 970, and a mounting block 956. The stylus insertion tool 955 is seen to have a nose 958, a heel 959, and a gap 960 therebetween. Tool 955 is seen to have top surface 963.

FIG. 14 illustrates lower tooling nest 600 with a tray 10, needles 470 and suture strands 490 positionally ready for the winding operation. FIG. 14 further illustrates the winding station 760, showing the stylus assembly 950 lowered as indicated by arrow 761 into position into the tray 10 in channel 11 in opening 269. The remaining upper tooling described hereinabove is not included in FIG. 14 view for visual clarity. The stylus base 980 and stylus assembly 950 have in between a controlled gap 953 of at least two diameters of the largest diameter suture to prevent potential damage thereto by preventing suture 490 from being pinched as they pass therebetween.

The stylus insertion tool 955 is positionally inserted into the suture track opening 269 in the channel 11 of tray package 10 to make the nose 958 and heel 959, and the gap 960 therebetween straddle the suture strands 490 extended thereacross.

Figure 15:
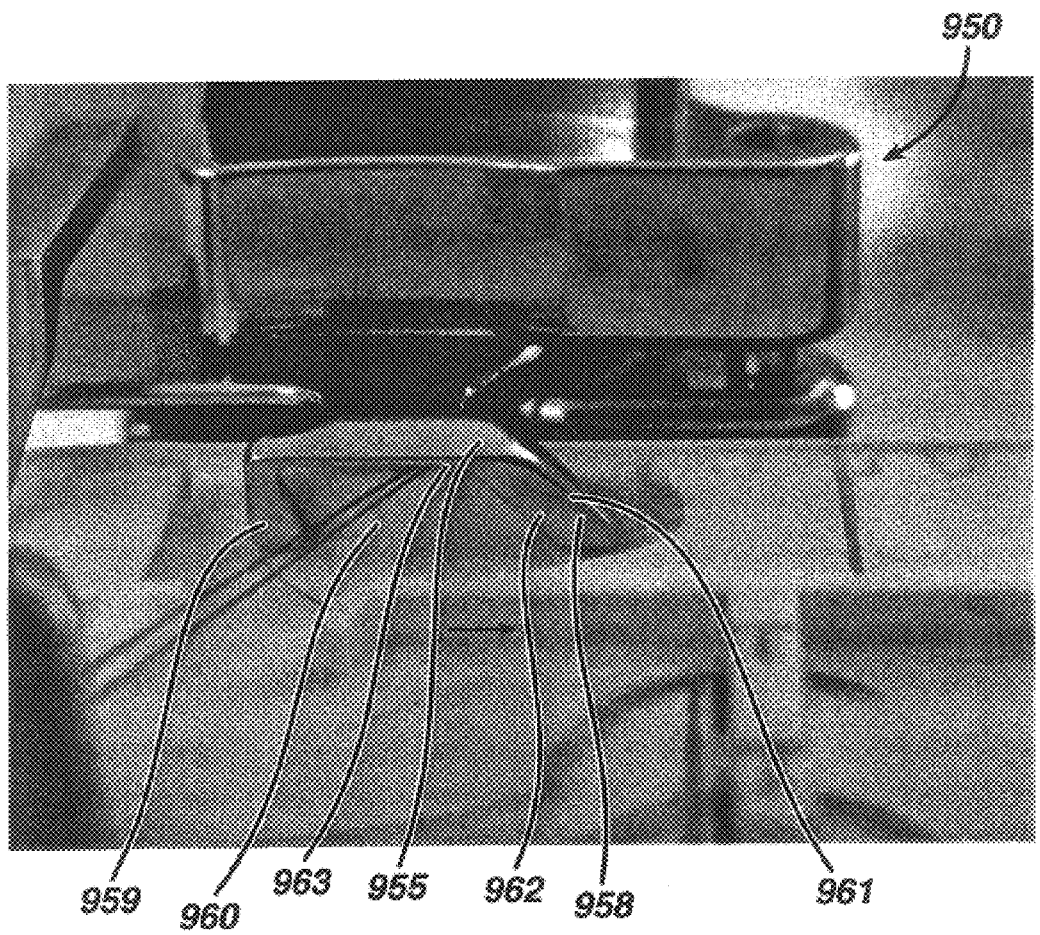
FIG. 15 is a magnified photograph of the package of FIG. 14 illustrating the stylus assembly inserted into a package suture channel opening.

FIG. 15 is an enlarged view of the stylus 955 of FIG. 14 in the package tray 10, illustrating the winding stylus 955 positioned in the suture channel opening 260 in suture channel 11 of package tray 10 prior to rotation of the tray 10 for the winding operation. The insertion tool 955 is positioned, placing the nose 958 and heel 959 straddling the suture strands 490 therebetween. The nose 958 is seen to have a front sloping plow surface 961, and a bottom surface 962. As the stylus 955 advances in the direction of arrow 762 relative to package 10, the nose plow surface 961 bears against the first cover flap member side 237, thereby plowing and cantilevering door member 230 upward and over top 963, and likewise continuing around the tray suture track 11. The insertion tool 955 guides the suture strands 490 into the suture channel 11, allowing the door flaps 230 to close behind to secure them from being dislodged or springing out.

Figure 16:
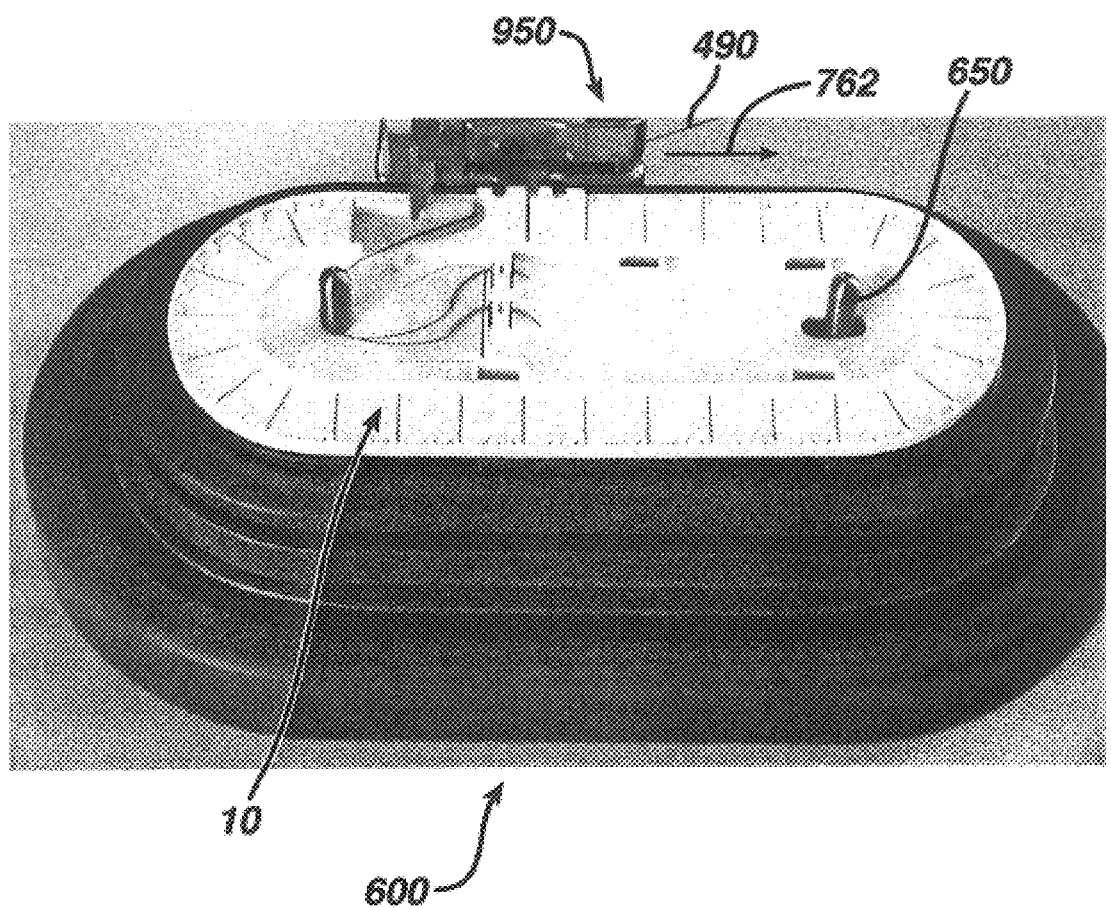
FIG. 16 is a photograph of the stylus and package of FIG. 14, illustrating the stylus advancing relative to the tray package in the suture channel, and opening cover door members as it advances in order to allow suture to be wound into the suture channel as the tray package is rotated in the tool nest.
Figure 17:
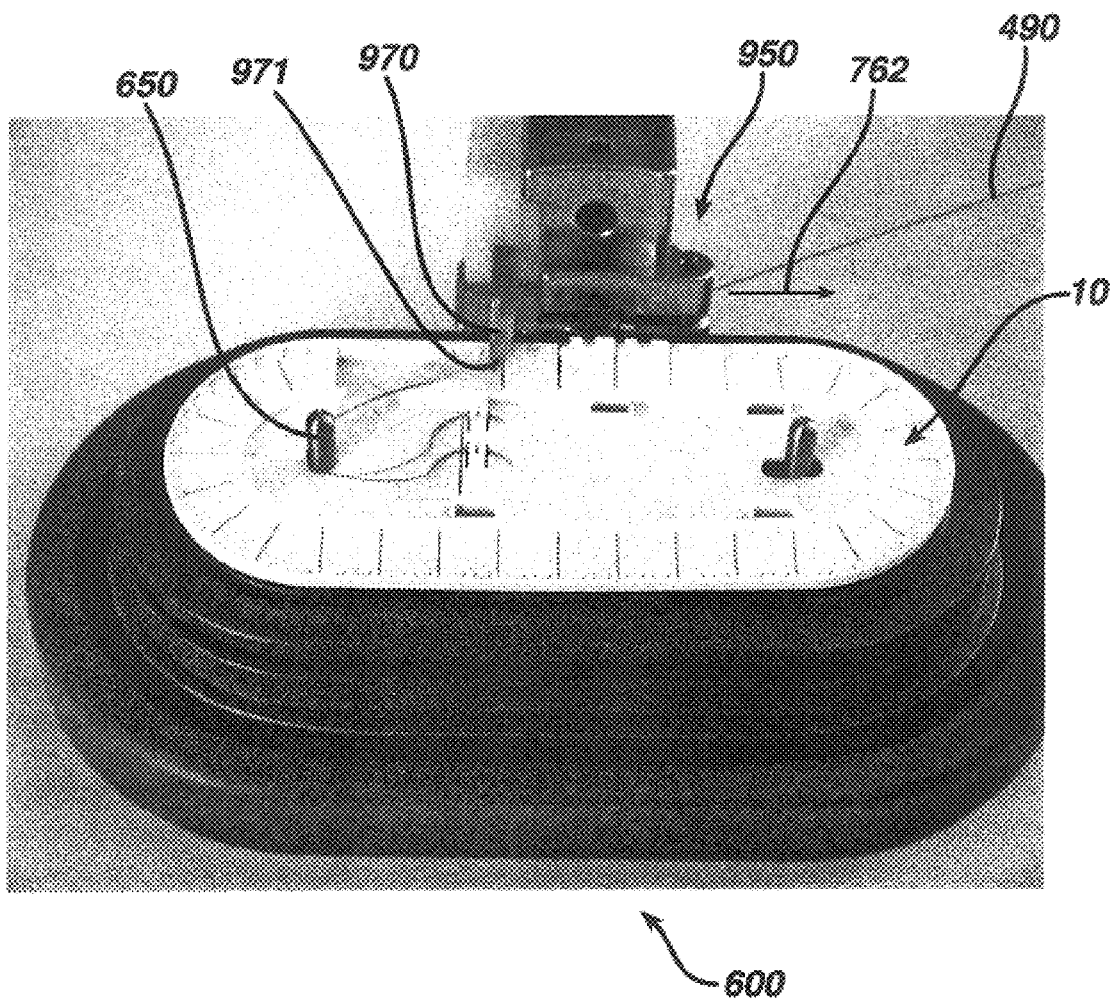
FIG. 17 is a photograph of the stylus, package and nest of FIG. 16 illustrating the stylus advancing in the suture track relative to the rotating tray package, and plowing cover doors open as it advances, and also illustrating the flap closure tool which subsequently moves the cover doors downward to the normally closed resting position.

FIGS. 16 and 17 further illustrate the cover door member 230 opening and inserting sequence as the stylus 955 is illustrated as it advances along the suture track 11 indicated by arrow 762. Flap closing tool 970, as seen in FIG. 17, has a ramp surface 971 that mechanically plows the flaps 230 down, thereby assuring that any that any flaps 230 which may have had insufficient memory in the living plastic hinge 239 to close on their own, are closed thereby. Flap closing tool 270 is integral with and positioned in close proximity behind the stylus insertion tool 955, extending down from frame 951, thereby quickly reverse plowing the flap 230, previously raised, down before the suture 490 trailing behind the stylus insertion tool 955 has an opportunity to come out of the suture channel 11.

Figure 18:
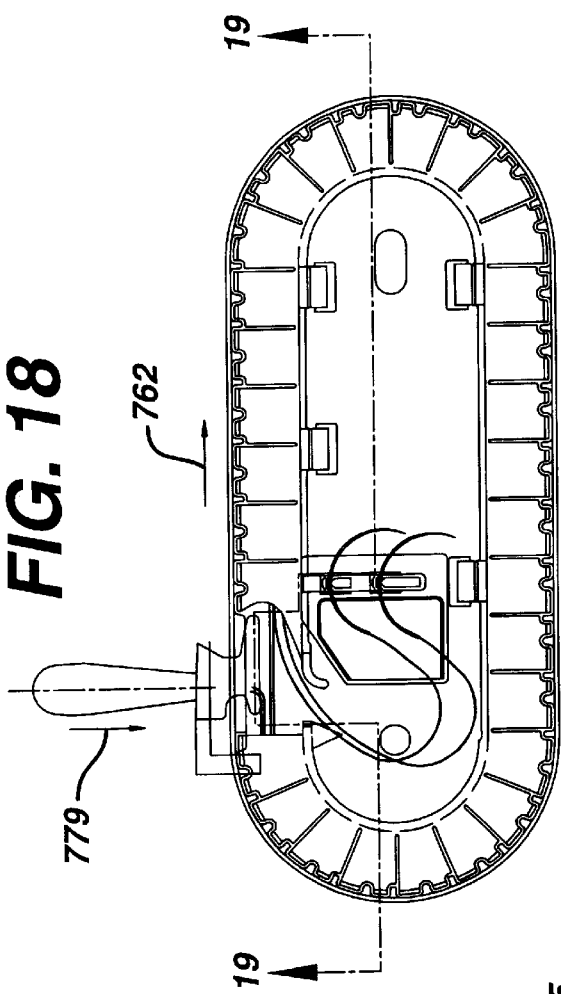
FIG. 18 is a plan view of the stylus in a tray package after the winding of the double-armed suture has been nearly completed, with the exception of the bottom of the suture loop.
Figure 19:
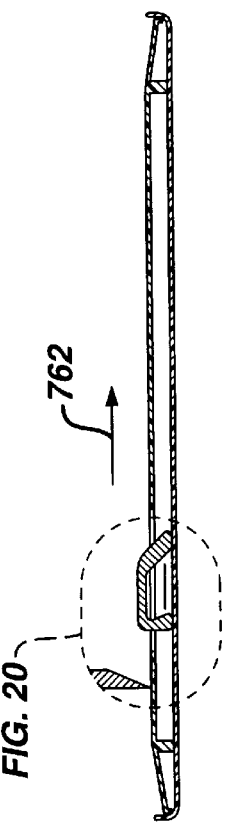
FIG. 19 is a side, cross-sectional view of the package of FIG. 18 taken along View Line 19—19 illustrating the stylus in the winding channel.
Figure 20:
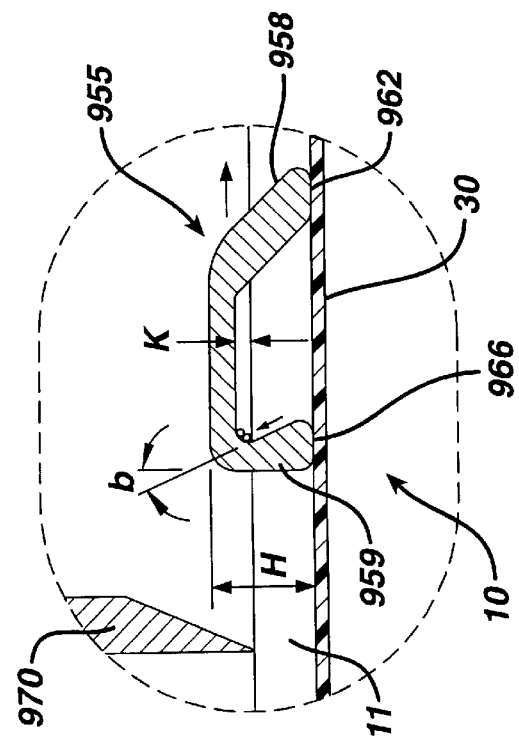
FIG. 20 is an enlarged cross-sectional view of the stylus of FIG. 19.

Additional details of the winding stylus 955 are illustrated in FIGS. 18, 19, and 20. FIG. 18 is a plan view of the package tray 10 that illustrates a stylus assembly 950 moving, during the winding operation at station 760, in the direction of arrow 762 with respect to the tray package 10, winding a double-armed suture 480. As winding progresses, the remaining unwound suture 490 in loop 495 advances in the direction of arrow 779 with respect to the stylus insertion tool 955. The suture material 490 enters the stylus 955 and is guided by the heel 959, under no tension, and gently layed onto the surface 31 of channel 11 parallel to the inner channel wall 210. On each lap or revolution around the suture track 11, the stylus insertion tool nose 958 plows adjacent suture strands 490 inwardly toward the package 10 center, thereby creating an orderly wind pattern, a requirement for friction free dispensing. The nose 958 and heel 959 are spaced apart, forming large gap 960 (also shown in FIG. 13) therebetween to allow passage of the suture loop 495 with no permanent distortion that might be retained in the shape memory of the suture material after dispensing in the operating room by the health care provider.

FIG. 19 is an elevation view of section 19—19 in FIG. 18, illustrating the stylus assembly 950 in suture channel 11 of package 955; a partial magnified view of the stylus assembly 950 of FIG. 19 in channel 11 is illustrated in FIG. 20.

As seen in FIG. 20, the stylus insertion tool 955 is illustrated sliding in the direction of arrow 762 on the suture track floor 31 with the nose 958 and heel 959 pressed with downward pressure of the stylus bottom surfaces 962 and 966 sufficient to embed the nose 958 and heel 959 below the surface plane 31 of said floor 30 into the flexible plastic tray material, thereby eliminating the possibility that an adjacent previously wound suture strand 490 could be run over and pinched or damaged by said nose 958 or heel 959. This enhances the ability of the package 10 and winding machine 500 to accommodate fine size sutures, as small as 8-0 (3 mil diameter).

The height "H" of the stylus 955, FIG. 20, is sufficient to effectively open the flaps 230 for suture insertion, but minimized beyond that to reduce stress and potential permanent deformation of the flap plastic hinges 239 (see FIG. 6).

The internal height "K" of the stylus ceiling 978 is greater than two suture diameters above the suture track outer wall 310 thereby effectively eliminating pinching or mechanical interference that might damage the sutures 490.

The heel 959 has a suture guiding surface 969. The suture guide surface 969 is sloped backward with a positive angle b, sufficient to effectively cause suture strands to climb upward in the direction of arrow 777 as they slide through said suture opening 960, minimizing scraping of the suture against the top 44 of the suture track outer wall 410.

All surfaces of the suture stylus assembly tool 950 are polished, free of surface irregularities, and shaped to avoid sharp edges, angles, or corners that could cause damage to the suture strands 490.

Figure 21:
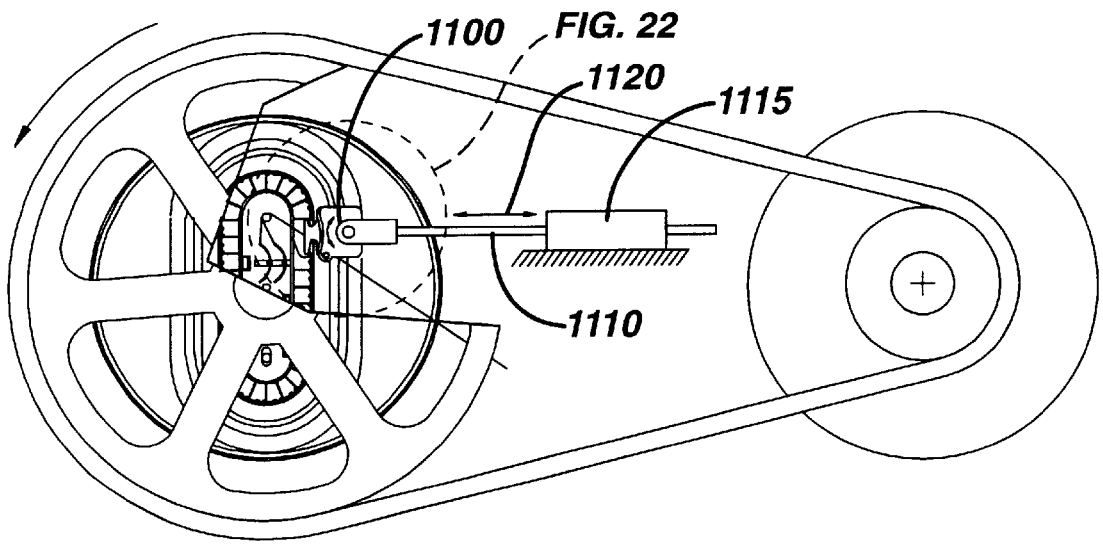
FIG. 21 is a top view of the winding station drive system of FIG. 12, diagrammatically illustrating the cam drive of the stylus.
Figure 22:
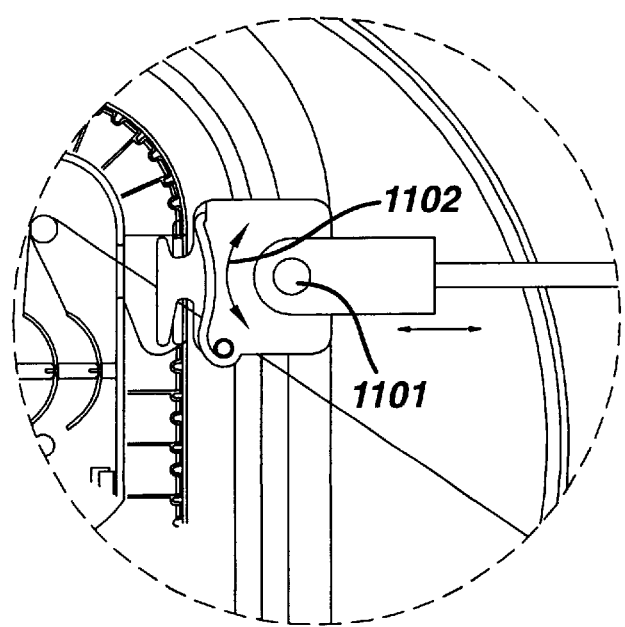
FIG. 22 is an enlarged view of the stylus of FIG. 21.

Referring now to FIG. 18, it can be seen that during the winding operation, winding stylus assembly 950 is precisely guided in the direction of arrow 762 with respect to tray 10, and parallel to the outer wall 40 of said tray guided by pins (not shown) in base 980 engaging grooves 990 (FIGS. 14 and 21) in the tooling base 600. As seen in FIGS. 21 and 22, the relative motion of the stylus 955 with respect to the package tray 10 illustrated in FIG. 18 is generated by rotation of the tray 10 in the direction of arrow 778 about its vertical axis 616 (FIG. 9).

The tool nest 600 containing package tray 10 is driven rotationally by the servomotor 763, timing belt 767, driving sprocket 767 and shaft 769 mounted thereto to, and lower tooling, all rotationally integral therewith. The stylus assembly 750 is guided by pins (not shown) engaged slidingly in grooves 990 in the lower tooling nest 600, and similar grooves and pins (not shown) in the upper tooling base.

The clevis 1100 is fixedly attached to an oscillating rod 1110 slidingly constrained by a linear bearing 1115 attached to the machine frame 510, and is thereby constrained to translate only in the directions generally radially in and out illustrated by arrows 1120. The stylus 950 is pivotally mounted thereto by a pin connection 1101, thereby free to rotate thereabout as indicated by arrow 1102.

It can therefore be seen that the mechanisms described hereinabove generate a motion, when lower tooling 600 is rotationally driven about its vertical axis 616, that causes the stylus insertion tool 955, straddling the suture strands 490, to progressively advance through the suture channel 11, relative to package 10, essentially following a path parallel to the periphery 35 of the package tray 10 outer wall 40.

The winding rotation described hereinabove continues for a sufficient number of turns to insert the entire length of suture 490 into the suture channel 11, and continue additionally until the stylus 955 is at the start position illustrated in FIG. 18, along with the assembly 950 and base 980. The winding tooling 1000 and assembly 950 are then raised, and the turret 540 (FIG. 9) is indexed for the next operation. The nests may rotate at speeds sufficient to efficiently and effectively wind suture into the suture channels, for example 50 rpm, however lower speeds or significantly higher speeds may be used. Correspondingly, the turret 540 will index in the preceding example at 20 cycle per minute, but may cycle more slowly or significantly faster to sufficiently provide for effective packaging.

Figure 23:
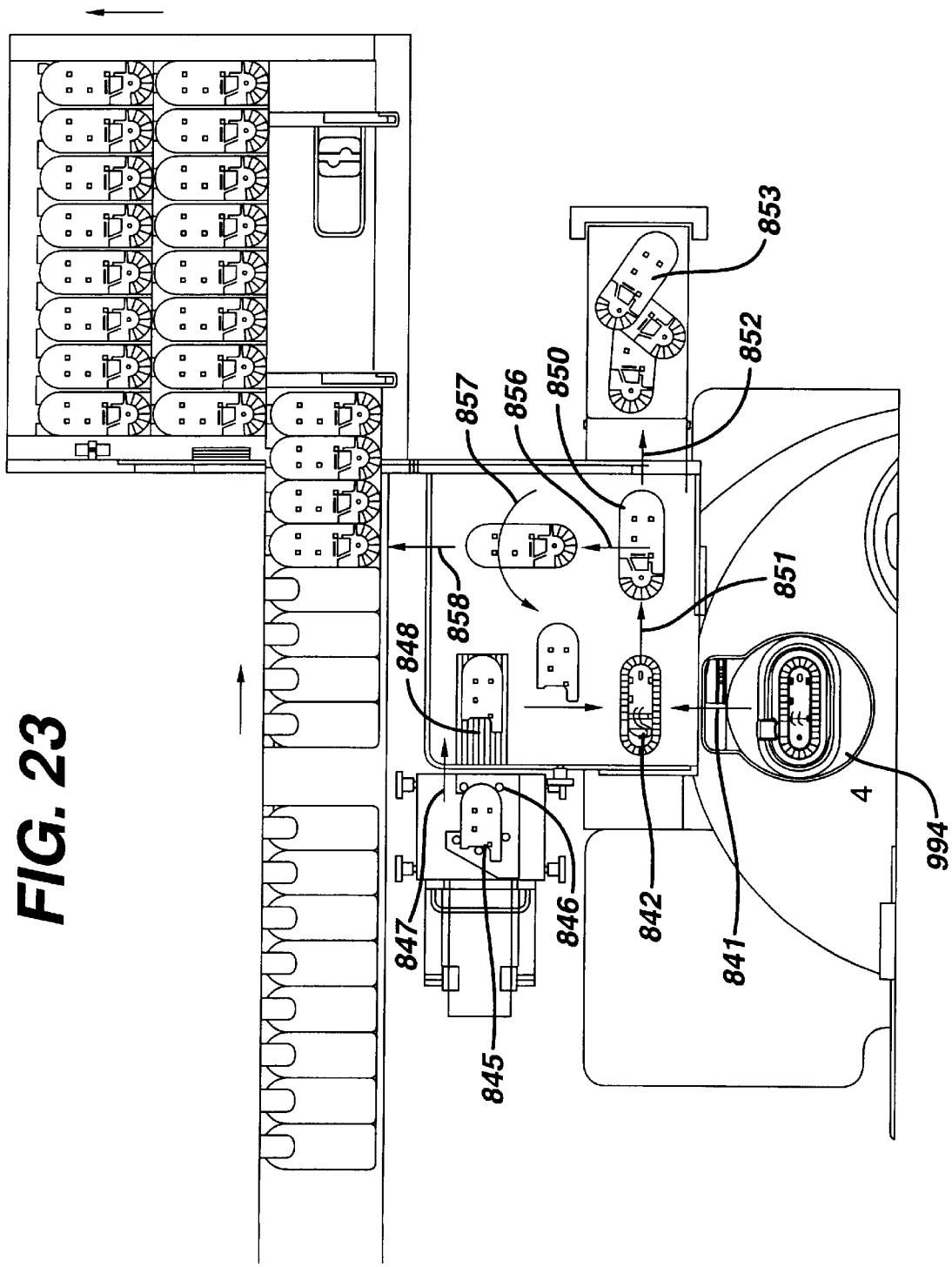
FIG. 23 is an enlarged, partial plan view of the packaging machine of FIG. 11 illustrating the machine 144 operations and process flow after a suture and surgical needles have been packaged in a suture channel package and indexed out of the winding station.

Now referring to FIG. 23 which illustrates an enlarged plan view of the rear section of the machine of FIG. 8, machine index station 994 of turret 540 is seen after indexing from the winding operation station 993, with the tray 10 having wound suture 490 contained therein. The machine index station 944 is aligned with package transfer station 800. At machine index station 994, the following operations take place utilizing transfers performed by various conventional slides and pick and place mechanisms. These devices may be actuated by air cylinders, lead screws driven by motors, servo or otherwise, and other techniques, utilizing vacuum cups or mechanical grippers to gain a hold on the package conventional in this art. These devices are custom designed, commercially purchased, or a combination thereof, and are known art in the machine design field. They are therefore not described in mechanical function, but by only the product transfer that is made, recognizing that a person knowledgeable in the design field would have a number of viable choices within the known art related to transfer devices to accomplish the desired result.

Figure 7:
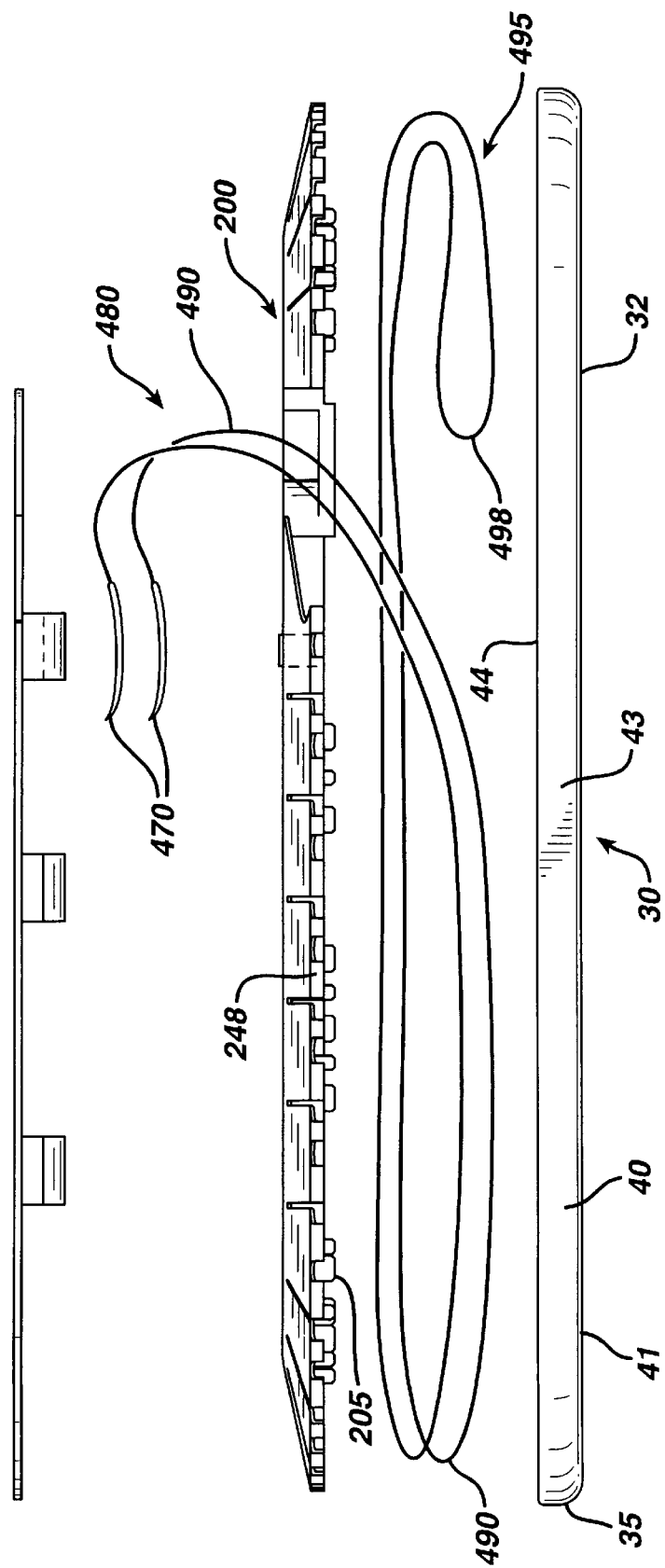
FIG. 7 is an exploded perspective view of the package of FIG. 3 illustrating the package base member, the suture channel cover member, a top cover member, and a double-armed suture.
Figure 24:
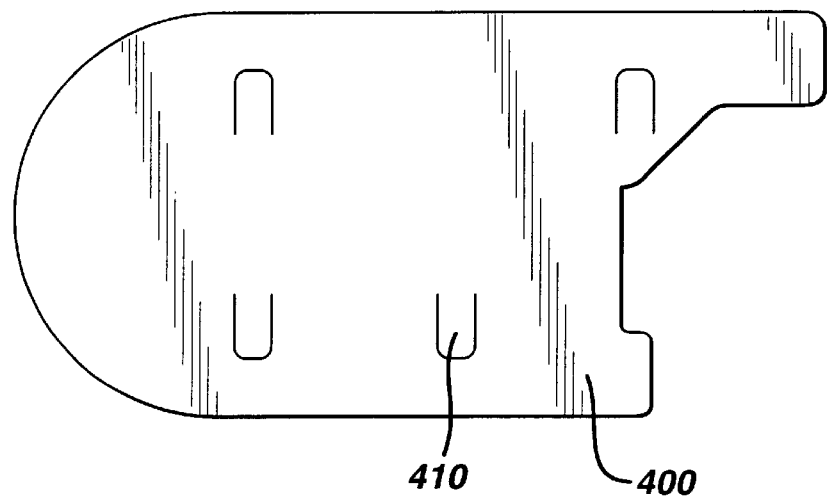
FIG. 24 is a top view of an optional top cover member that may be mounted to a package of the present invention after a surgical needle and sutures have been packaged.
Figure 25:
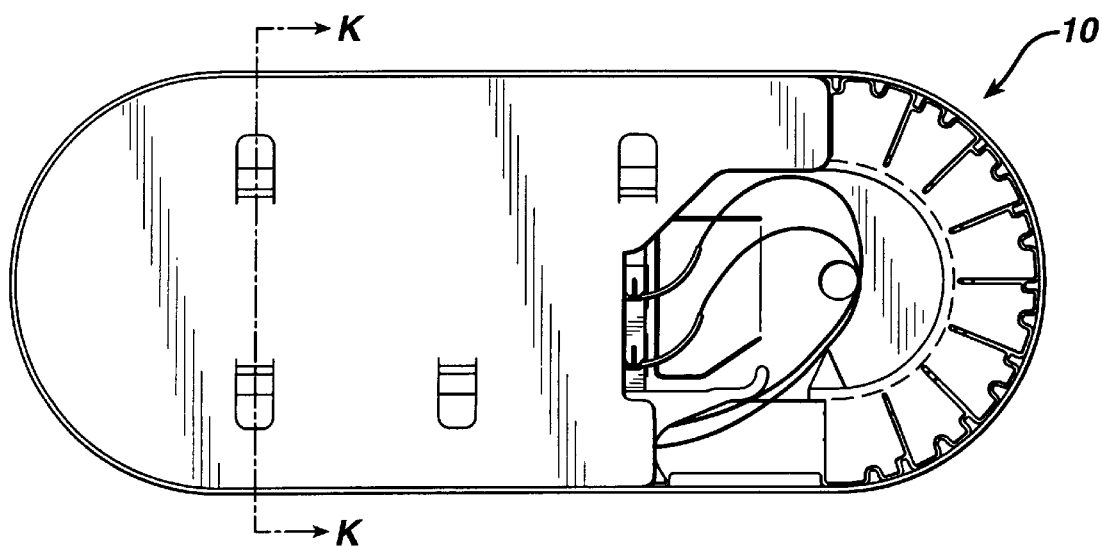
FIG. 25 is a top view of a package having a double-armed suture therein after it has been processed using a packaging machine and process of the present invention, illustrating the top cover of FIG. 25 mounted to the top thereof.

The next assembly requirement is to fixedly place a top cover 400 on the loaded tray 10, as briefly shown in FIG. 7, at the lid assembly station 840. Said cover 400 serves to protect the double-armed suture 480, and provides a planer surface for printed label information. FIG. 24, illustrates the cover 400, and FIG. 25 illustrates the tray 10 with the cover 400 mounted thereto.

Figure 26:
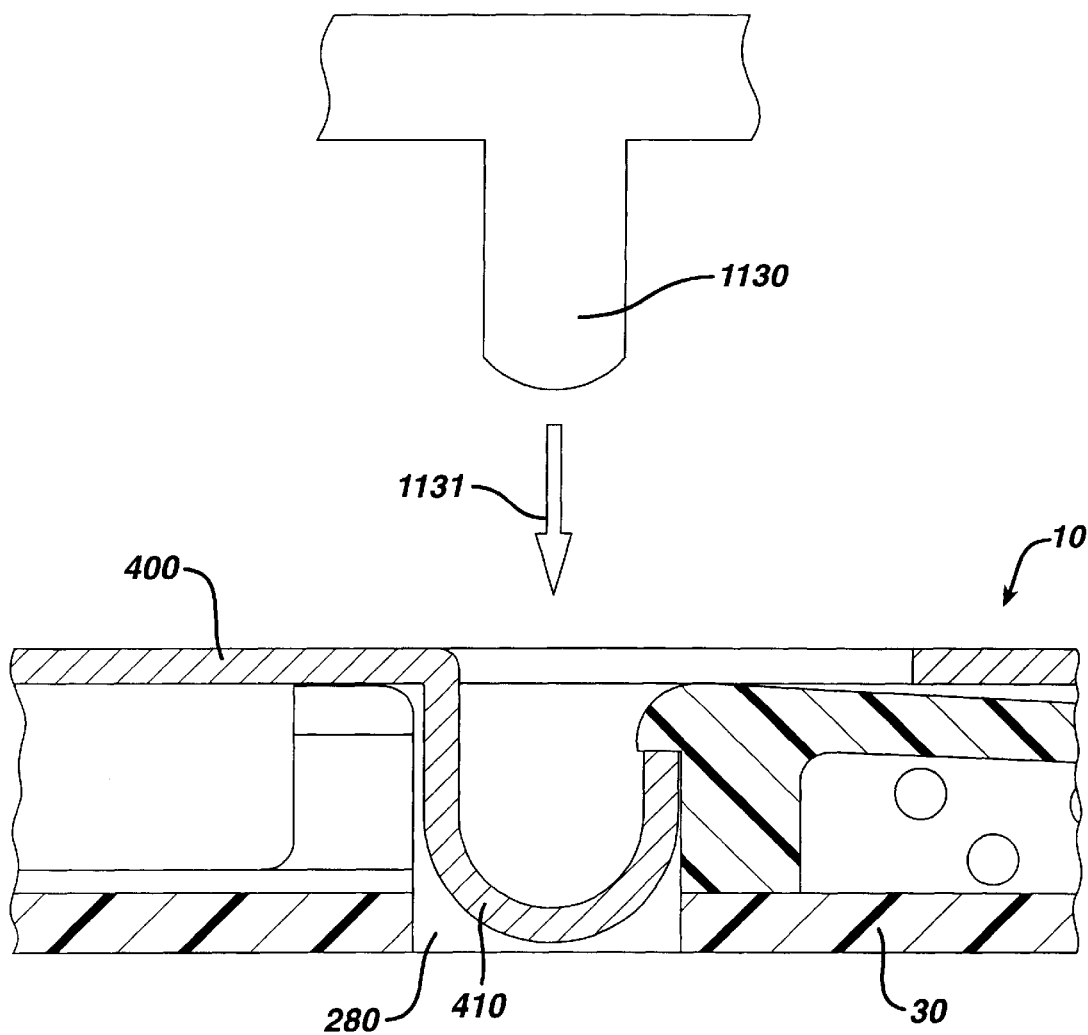
FIG. 26 is a partial magnified cross-sectional view taken along View Line K—K, diagrammatically illustrating the insertion a cover tab of a top cover member into a latch in the package of FIG. 25.

The cover 400 is attached at lid assembly station 840 to the tray molding 10 by staking a plurality of tabs 410 into molded cleat receptacle openings 280 in said tray 10 utilizing the following process. Referring to FIG. 26, which illustrates a section K—K through the mounted or staked tab 410 of FIG. 25. The paper cover 400, shown in enlarged cross-section, is placed upon the package tray 10, also shown in enlarged cross-section. Each of the tabs 410 are positionally placed on the cover 400 to align with corresponding molded openings 280 therebeneath, said holes openings 280 illustrated in FIGS. 2a–d.

Referring again to FIG. 26, a staking tool 1130 is seen positioned above each of the paper cover tabs 410, and as it descends vertically downward, in the direction of arrow 1131, it causes the radiused nose 1134 to deform the tab 410 to form down into the tray opening 280 until the tab end 411 has snapped past and sprung under the cleat retention member 289, thereby securing said tab 410. The plurality of tabs 410, latched in this manner, secure the paper cover 400 to the package tray 10.

The machine assembly sequence for the top cover assembly is illustrated in FIG. 23. At package transfer station 800, the wound tray 10 is mechanically picked from tool nest 600, preferably utilizing a robotic mechanical gripper (not shown), raised to clear the tool nest 600, translated in the direction of arrow 841, lowered, and released to a precise location 842 at lid assembly station 840.

From lid hopper and feeding station 820, covers 400 are fed from a vertical stack 845, FIG. 23, the hopper containment thereof formed by a plurality of open vertical rods 846. A vacuum ported slicing shuttle slide (not shown) below said hopper stack feeds one paper cover per machine cycle from the bottom of the stack, as indicated by arrow 847, depositing said cover 400 in precise location on a vacuum plate 848. The cover 400 is precisely translated by a vacuum gripper (not shown) and placed precisely on the awaiting package tray 10. The spring mounted vacuum pickup tool (not shown) comprising vacuum cups, and also an appropriate number and location of staking tools described hereinabove (FIG. 26), mounted to emerge upon overtravel downward of the vacuum tool, transports the cover, and stakes it, upon the said overtravel, to the tray 10, thereby securing the cover 400 and producing a completed package assembly.

A lateral shuttle device (not shown) transports the completed package assembly as illustrated by arrow 851 to the accept/reject position 850.

If the package 10 has been electronically flagged in the programmable controller as defective, a mechanical element at this station 850 causes the package to be transported, indicated by arrow 852, into the scrap box 853. The defective signal could originate from the electronic control system due to a missing or out of place component, automatically detected in the operations upstream, or by a human operator observing a faulty operation.

A package accepted at the accept/reject station 850 is transported to magazine load station 860 by a linear pick and place mechanism that is moved in the direction of arrow 856, then a 90° rotation motion in the direction of arrow 857, transported per arrow 858, lowered, and released into position, forming a stack 861 into magazine compartment 863 in magazine 865.

Magazines 865 are filled with a plurality of packages 10, and indexed one compartment pitch at a time as indicated by arrow 869, until the magazine 865 is full.

The next empty magazine 865 is indexed into the appropriate position behind the magazine 865 being filled, thereby allowing uninterrupted cycling of the machine 500. Filled magazines 865 are shuttled as indicated by arrows 869 and 881 along the machine top plate 160 by suitable advance mechanisms thereunder acting on ribs in the magazine base (not shown).

The packages 10 containing the double-armed sutures 480 may then be further processed by placement in conventional outer pouch or package for conventional sterilization treatments such as gaseous steriliants, autoclaving, radiation and the like. When used by the surgeon in a surgical procedure, the package 10 is placed into a sterile field. Using a conventional needle grasper, the surgeon pushes down lifting tab 300 partially into opening 150 and the needles 550 are grasped and removed from the needle park members 350. The needles 40 and suture 490 are then pulled away from the package 10 and suture 490 exits through exit port 260 and channel exit 269, and then from channel 11.

The packaging machines and processes of the present invention, surprisingly and unexpectedly, allow the high speed winding of double-armed surgical sutures in tray packages. This is accomplished while maintaining the integrity of the sutures and preventing them from being damaged. The packages and processes produce a high quality packaged product, while eliminating manual packaging steps.

Although this invention has been shown and described with respect to detailed embodiments thereof, it will be understood by those skilled in the art that various changes in form and detail thereof may be made without departing from the spirit and scope of the claimed invention.

We claim:

1. A machine for winding suture into a suture tray package comprising:
   a machine frame having a top, a bottom, sides and an interior;
   a disc member rotatably mounted to the top of the frame, said disc member having a periphery, top, a bottom and a side about the periphery of the disc member;
   a plurality of tool nests, each tool nest rotatably mounted to the top of the disc member, said tool nests comprising:
   a nest frame, having a top, a bottom and sides; and,
   at least two winding pin members extending up from the top of the nest frame;
   a rotatable tool mounted to the machine frame, said tool being displaceable downwardly to engage with the pin members on the nest frame, such that rotation of the tool will rotate the tool nest; and,
   a stylus member movably mounted to the machine frame, for cooperation with the tool nests, comprising:
   a stylus frame having a top, sides and a bottom;
   a stylus mounted to the bottom of the stylus frame having a front nose member and a rear heel member separated by a suture opening, said stylus having a top surface; and,
   a door closing member extending down from the bottom of the stylus frame adjacent to the stylus.

2. The combination of a suture tray package and a packaging machine, comprising
   I. a packaging machine comprising:
      a machine frame having a top, a bottom, sides and an interior;
      a disc member rotatably mounted to the top of the frame, said disc member having a periphery, top, a bottom and a side about the periphery of the disc member;
      a plurality of tool nests, each tool nest rotatably mounted to the top of the disc member, said tool nests comprising:
      a nest frame, having a top, a bottom and sides; and,
      at least two winding pin members extending up from the top of the nest frame;
      a rotatable tool mounted to the machine frame, said tool being displaceable downwardly to engage with the pin members on the nest frame, such that rotation of the tool will rotate the tool nest; and,
      a stylus member movably mounted to the machine frame, for cooperation with the tool nests, comprising:
         a stylus frame having a top, sides and a bottom;
         a stylus mounted to the bottom of the stylus frame having a front nose member and a rear heel member separated by a suture opening, said stylus having a top surface; and,
         a door closing member extending down from the bottom of the stylus frame adjacent to the stylus; and
   II. a suture tray package comprising:
      a flat base member having a top and an outer periphery;
      an outer wall extending up from the base member about the periphery of the base member;
      an inner wall, interior to the outer wall, extending up from the top of the base member, said inner wall having a top and said inner wall space away from the outer wall to form a suture channel;
      a plurality of doors extending from the top of the inner wall over the winding channel; and,
      at least two needle park members extending up from the top of the base member, said needle park members located interior to the inner wall,
      wherein the tray package is mounted in the tool nest.

3. A method of winding a double armed suture in a tray package, the method comprising:
   I. providing a tray package, the tray package comprising:
      a flat base member having a top and an outer periphery;
      an outer wall extending up from the base member about the periphery of the base member;
      an inner wall, interior to the outer wall, extending up from the top of the base member, said inner wall having a top and said inner wall space away from the outer wall to form a suture channel;
      a plurality of doors extending from the top of the inner wall over the winding channel; and,
      at least two needle park members extending up from the top of the base member, said needle park members located interior to the inner wall;
   II. providing a packaging machine, the packaging machine comprising:
      a machine frame having a top, a bottom, sides and an interior;
      a disc member rotatably mounted to the top of the frame, said disc member having a periphery, top, a bottom and a side about the periphery of the disc member;
      a plurality of tool nests, each tool nest rotatably mounted to the top of the disc member, said tool nests comprising:
      a nest frame, having a top, a bottom and sides; and,
      at least two winding pin members extending up from the top of the nest frame;
      a rotatable tool mounted to the machine frame, said tool being displaceable downwardly to engage with the pin members on the nest frame, such that rotation of the tool will rotate the tool nest; and,
      a stylus member movably mounted to the machine frame, for cooperation with the tool nests, comprising:
         a stylus frame having a top, sides and a bottom;
         a stylus mounted to the bottom of the stylus frame having a front nose member and a rear heel member separated by a suture opening, said stylus having a top surface; and,
         a door closing member extending down from the bottom of the stylus frame adjacent to the stylus.
   III. providing a double-armed surgical suture comprising a suture having opposed ends, and having a surgical needle mounted to each end;
   IV. mounting the surgical needles in the needle parks; and
   V. indexing the disc to a winding station where the rotatable tool is located, engaging the nest with the rotatable tool, inserting the stylus into the suture channel, and rotating the tool nest and package to wind the suture in the suture channel.

* * * * *